United States Patent
Benabid et al.

(10) Patent No.: US 9,033,897 B2
(45) Date of Patent: May 19, 2015

(54) METHOD FOR DETERMINING THE MOLECULAR COMPOSITION OF A TARGET TISSUE OR ANOTHER BODY STRUCTURE, AND ITS DIAGNOSTIC APPLICATIONS

(75) Inventors: Alim-Louis Benabid, Meylan (FR); Ali Bouamrani, Grenoble (FR); Jean-Paul Issartel, Saint-Egrève (FR); David Ratel, Montagnole (FR); Francois Berger, Meylan (FR)

(73) Assignee: INSTITUTE NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 1684 days.

(21) Appl. No.: 11/795,119

(22) PCT Filed: Jan. 16, 2006

(86) PCT No.: PCT/IB2006/000064
§ 371 (c)(1),
(2), (4) Date: Sep. 20, 2007

(87) PCT Pub. No.: WO2006/090220
PCT Pub. Date: Aug. 31, 2006

(65) Prior Publication Data
US 2009/0280523 A1    Nov. 12, 2009

Related U.S. Application Data

(60) Provisional application No. 60/643,592, filed on Jan. 14, 2005.

(30) Foreign Application Priority Data

Jan. 31, 2005  (EP) ..................................... 05075232

(51) Int. Cl.
| | |
|---|---|
| A61B 10/00 | (2006.01) |
| A61B 10/02 | (2006.01) |
| A61B 17/32 | (2006.01) |
| A61B 17/3207 | (2006.01) |
| B01L 3/00 | (2006.01) |

(52) U.S. Cl.
CPC ..... *A61B 10/02* (2013.01); *A61B 2017/320008* (2013.01); *A61B 2017/320012* (2013.01); *A61B 2010/0216* (2013.01);
(Continued)

(58) Field of Classification Search
CPC .............. A61B 17/320708; A61B 17/320004; A61B 17/320064; A61B 2010/0216; A61B 2017/320008; A61B 2017/320012; B01L 3/50; B01L 3/5029
USPC .................................. 600/562, 569, 570, 572
See application file for complete search history.

(56) References Cited

U.S. PATENT DOCUMENTS

| | | |
|---|---|---|
| 3,857,384 A | 12/1974 | Watson |
| 3,877,464 A | 4/1975 | Vermes et al. |

(Continued)

OTHER PUBLICATIONS

"Introduction a la Biologie Moleculaire de la Cellule"; *Medecine-Sciences Flammarion Ed.*, 1999; pp. 159 & 160.

*Primary Examiner* — Devin Henson
(74) *Attorney, Agent, or Firm* — Oliff PLC

(57) ABSTRACT

The present invention relates to a sampling instrument adapted for taking a sample in situ and in vivo or taking a sample ex vivo of a target tissue or body structure, in a maximum quantity of less than $10^{-6}$ g, the instrument comprising an elongated active member (10) with a distal operative end (11) having at least one retaining surface (12) arranged for contacting directly the target tissue or body structure, capturing and retaining molecules of the target tissue or body structure thereto.

21 Claims, 9 Drawing Sheets

(52) U.S. Cl.
CPC ....... *A61B 17/320708* (2013.01); *B01L 3/5029* (2013.01); *B01L 3/50* (2013.01)

(56) References Cited

U.S. PATENT DOCUMENTS

| | | |
|---|---|---|
| 3,995,618 A | 12/1976 | Kingsley et al. |
| 5,129,402 A | 7/1992 | Koll et al. |
| 5,330,422 A * | 7/1994 | Schneider ................ 604/27 |
| 5,543,115 A * | 8/1996 | Karakawa ................ 422/535 |
| 5,830,154 A | 11/1998 | Goldstein et al. |
| 6,155,990 A | 12/2000 | Fournier et al. |
| 6,921,370 B2 * | 7/2005 | Zhou et al. ................ 600/562 |
| 2002/0095073 A1 * | 7/2002 | Jacobs et al. ................ 600/300 |
| 2003/0028123 A1 | 2/2003 | Pevoto |

\* cited by examiner

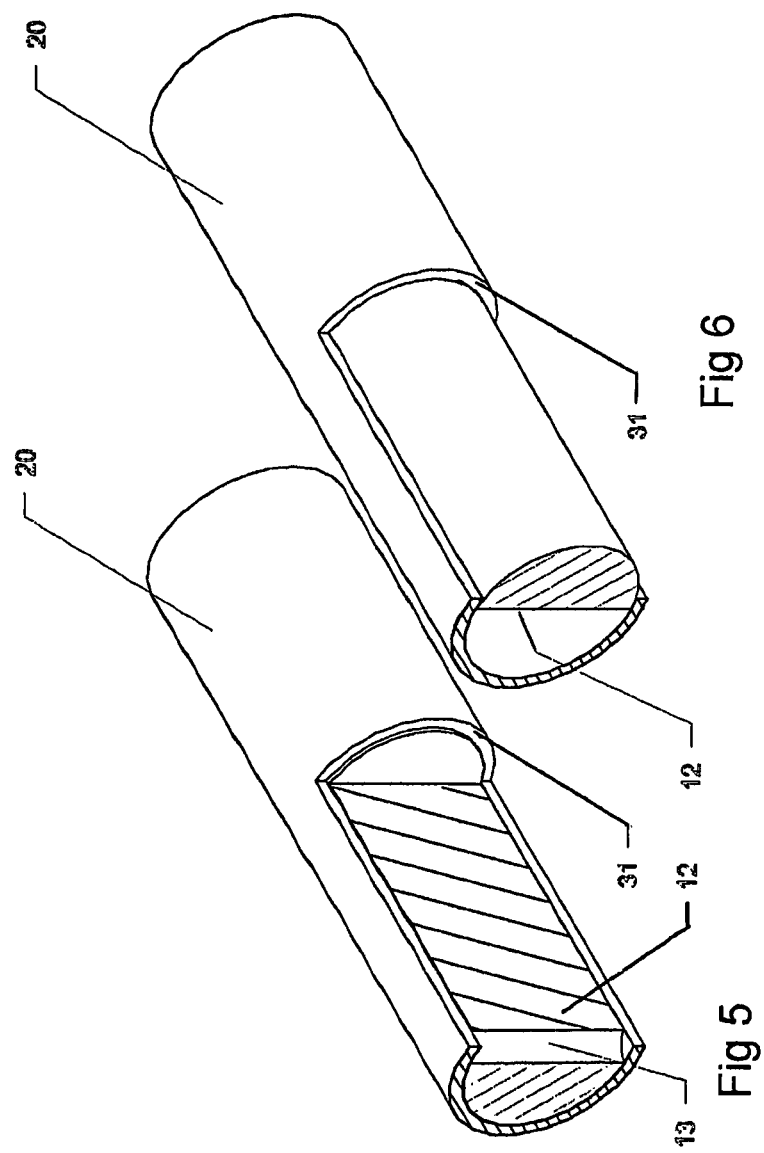

Comparison of the method for determining the molecular composition of a fingerprint taken *in situ* or *ex vivo* according to the present invention with prior art methods (invasive + multiple steps)

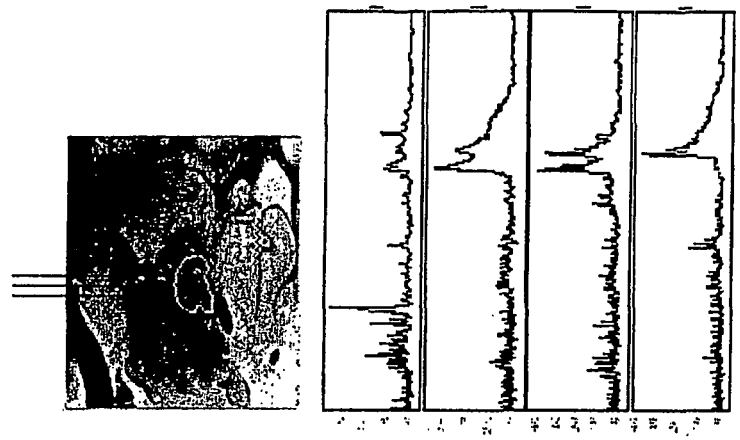
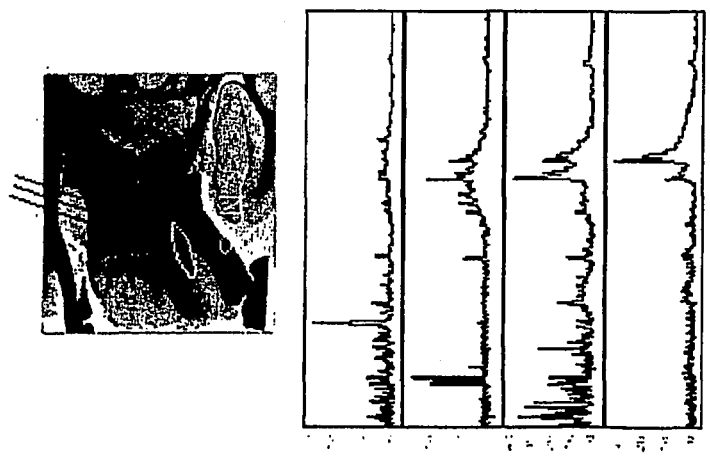
FIG. 13

METHOD FOR DETERMINING THE MOLECULAR COMPOSITION OF A TARGET TISSUE OR ANOTHER BODY STRUCTURE, AND ITS DIAGNOSTIC APPLICATIONS

TECHNICAL FIELD

This invention relates to the medical field, in particular the diagnostic field.

The apparatus and methods of the present invention have applications in biology, in particular in molecular biology, in diagnosis and in surgery.

BACKGROUND OF THE INVENTION

Medicine presently substantially relies on pathological examination method, which consists in taking a piece of pathological tissue to ultimately arrive at a diagnosis of a pathological condition, whether infectious, tumoral, viral, etc. . . . The pathological diagnosis has to be carried out on biopsies, which are coloured, then examined under a microscope. The pathological diagnosis is thus the result of an observation with a microscope.

A surgical operation is therefore required to sample the pathological tissues, each time implying potential secondary functional consequences or damages which can be tragic, in particular on the brain.

To minimize these side effects, increasingly microinvasive surgical methods have been designed like, for example, intracerebral stereotactic biopsies.

These microinvasive approaches have been developed in all fields of human pathology (breast microbiopsy, hepatic biopsy . . . ).

Although they are essential for reducing iatrogenicity in surgical operations, they make anatomopathologic diagnosis more difficult compared to conventional sampling which provides macroscopic pieces which can be analyzed more easily.

Furthermore, the understanding of the molecular mechanisms of an increasing number of human pathological diseases has led to the emergence of non-microscopic, supplementary markers which replace or supplement the anatomopathologic diagnosis.

Thus there is a present need in the art to go beyond the limits of conventional anatomopathologic diagnosis.

A great number of prior art documents (e.g. U.S. Pat. Nos. 3,857,384, 6,155,990, 3,877,464, etc. . . . ) relate to devices adapted to be inserted into the vaginal canal and cervix area in order to obtain a specimen that can, thereafter be analysed and tested. According to these devices, it is necessary that tissue cells from the cervical area be obtained, and that the cells be examined under a microscope.

It is an object of the present invention to capture and retain molecules, more particularly protein in a maximum quantity of less than $10^{-6}$ g, in order for the method and instrument to be qualified as non invasive. Accordingly, the sampling instrument of the present invention is adapted to be as less invasive as possible. The sampling instrument of the present invention notably presents an external diameter that makes it adapted to be as less invasive as possible. It is to be understood that the sampling instrument of the present invention may capture and retain some cells. However first it is not the object to the present invention and second the conservation of theirs integrities is not expected, unlike prior art devices.

SUMMARY OF THE INVENTION

This invention provides apparatus and methods for determining the detailed molecular composition of a target tissue or another body structure of a human or animal body. This invention also provides a method for obtaining a molecular fingerprint of this tissue or organ. The methods of the present invention do not rely on taking a piece of tissue, but on collecting a molecular fingerprint or trace of that tissue and using it as a diagnostic raw biological material, thereby replacing the conventional anatomopathologic examination.

According to the present invention, molecular fingerprinting approaches have been developed for implementing a complex molecular pathological phenotyping by studying, for example, the transcriptomic profile using oligonucleotide microarrays or the complex proteomic profile of the fingerprint by mass spectrometry or other appropriate sensitive techniques.

According to the present invention, there is provided a sampling instrument for taking a sample in situ or ex vivo and an apparatus which comprises said sampling instrument. The present invention also relates to an instrumented analysis chain comprising said sampling instrument or said apparatus. The sampling instrument is particularly adapted to molecular fingerprinting the target tissue or other body structure, i.e. for taking fingerprints on the molecules, preferably proteins that are available at the target location in or on the target tissue or body structure. The sampling instrument is adapted to take a trace, i.e. a very small amount, usually one quantitatively assessable with current biological techniques for assays of molecular components.

The methods of the present invention may be used to improve timeliness, effectiveness, accuracy and overall benefit-to-cost ratio for determining the qualitative and possibly quantitative molecular composition of a target tissue or other body structure.

In its broader aspect, a method according to the present invention comprises the following steps:

a) contacting directly a target tissue or body structure with a retaining surface, so as to take a sample on said tissue or body structure in a quantity at least equal to the sensitivity threshold of the molecular analysis means of step c); preferably said quantity is less than $10^{-6}$ g, in particular less than $10^{-9}$ g, for example less than $10^{-15}$ g;

b) optionally treating the sample so captured and retained, for example in a non denaturing and/or disrupting manner;

c) determining the qualitative and/or quantitative molecular composition of said sample, using molecular analysis means.

It is to be noted for the sake of clarity that apposing said retaining surface with said tissue or body structure amounts to contacting said surface with said tissue or body structure.

The chemical surface of the retaining surface makes it possible to capture and retain molecules from the target tissue or body structure. Said molecules are thereafter taken off from the retaining surface by the means of various solutions and analysed with analysis means.

The sample may be taken in situ and in vivo, or ex vivo, as hereunder defined, from said target tissue or body structure.

According to a preferred embodiment:
- the determination of the molecular composition of the sample is made with said sample remaining or having remained on the retaining surface,
- or all steps a) to c) are carried out with a same support comprising the retaining surface.

With the help of a sampling instrument as hereunder defined and described, the retaining surface is contacted with said tissue or said structure in a manner such as pressing and/or rubbing it for a duration sufficient to take off a sample quantity that can be detected and resolved by the molecular analysis means.

If required, all the contacting parameters are determined, by submitting the quantity taken off to the molecular analysis means, and analysing the output signals to determine the presence of retrievable molecular species or entities such as proteins.

Said molecular analysis is implemented directly on said sample, i.e. without any intermediate treatment other than preparing it to said molecular analysis.

BRIEF DESCRIPTION OF THE DRAWINGS

The following figures make it possible to illustrate the subject of the invention but do not limit the scope thereof in any way.

FIG. 5 and FIG. 6 are section views of the active member of the sampling instrument shown on FIG. 1, respectively in the open position and in the closed position of the elongated hollow member;

FIG. 12 to 16 are described in the examples of the present invention.

DETAILED DESCRIPTION OF THE INVENTION

Definitions

Figure 1:
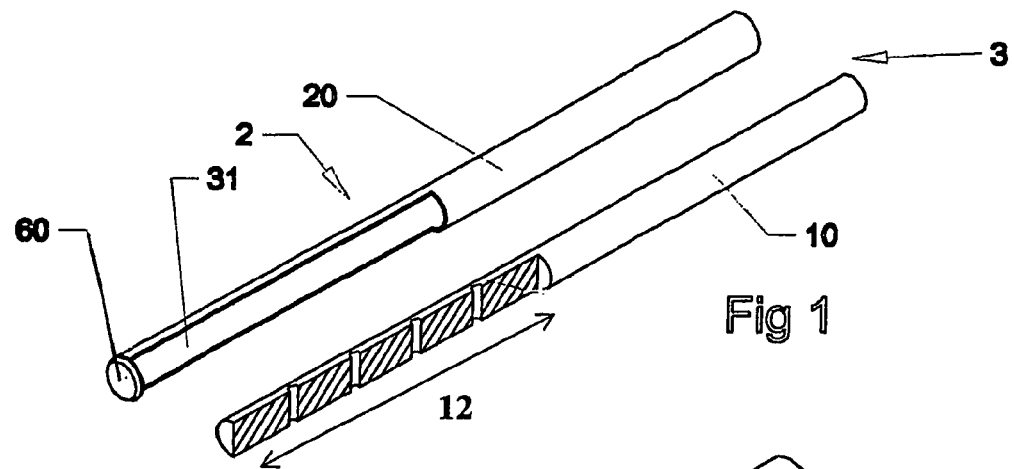
FIG. 1 details an arrangement of the sampling instrument of the present invention in perspective view.

The terms used in this specification generally have their ordinary meaning in the art, within the context of the invention, and in the specific context where each term is used. Certain terms are discussed below, or elsewhere in the specification, to provide additional guidance to the practitioner in understanding the apparatus and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

"Anatomopathology" refers to the subspecialty of pathology that pertains to the macroscopic and microscopic study of organs and tissues removed for laboratory diagnosis in surgical operation or biopsy or during a post-mortem examination, and also the interpretation of the results of such study.

In accordance with the present invention, molecular biology definitions lie within the skill of the art. Such techniques are explained fully in the literature.

"Protein" relates to a large molecule composed of one or more chains of amino acids in a specific order; the order is determined by the sequence of nucleotidic bases in the gene that codes for the protein. Proteins are required for the structure, function, and regulation of the body's cells, tissues, and organs; and each protein has unique functions. Examples are hormones, enzymes, and antibodies.

"Proteome" refers to the proteins expressed by a cell or organ at a particular time and under specific conditions, while "transcriptome" refers to the full complement of activated genes, mRNAs, or transcripts in a particular tissue at a particular time. "Proteomics" refers to the study of the full set of proteins encoded by a genome. Proteome analysis is the measurement of protein expression in a biological sample/specimen to characterize biological processes, such as disease and mechanisms of gene expression. Protein expression is crucial as a diagnosis tool.

The term "microarray" means a set of miniaturized elementary areas or spots of reaction or interaction that may be used to test DNA fragments, antibodies, or proteins. The microarray technology consists, generally, of probe sites or molecules being attached to a solid substrate, and in contracting the target molecules, obtained from cell lysates with the probe molecules or sites. Sometimes, target molecules are labeled prior to exposure to the microarray. Once exposed to the microarray, some target molecules selectively form probe/target pairs by binding/hybridizing with the complementary probe molecules on the microarray. The target molecules that do not form pairs are removed from the microarray. Where the probe/target pairs are formed on the microarray, the scientist can then visualize the probe molecules which have interacted with labelled target molecules.

The terms "target tissue or other body structure" relate to any structural or functional unit of the human or animal body which is likely to be of interest, in particular for diagnosis purposes. As a way of example, it is an organ, i.e. a fully differentiated structural and functional unit that is specialized for some particular function, for example the brain, the liver, the lungs, the spleen.

According to the present invention, the target tissue is possibly a tumor. The term "tumor" means an abnormal mass of tissue due to excessive cell division. Tumors perform no useful body function (has no physiological function). They may be either malignant (cancer) or benign (not cancer). A malignant tumor is a cancer that can spread to other parts of the body while a benign tumor does not spread in most cases.

The terms "other body structure" refers for example to specific anatomic domains that are easily accessible for sample such as skin, mucosae, or contain cavities or vessels such as venous-cardiac system, digestive tracts, uro-genetical tracts, or to biological fluids such as physiological fluids like arterial or venous blood, CSF, or non physiological or pathological fluids like cystic fluids in tumors, pleural effusion, ascitis.

The terms "in vivo" means within a living organism or body, either a human body or a non-human animal body.

Non-human animals include, without limitation, laboratory animals such as mice, rats, rabbits, hamsters, guinea pigs, etc.; domestic animals such as dogs and cats; and, farm animals such as sheep, goats, pigs, horses, and cows; for experimental purposes, these non-human animals may be genetically modified or transformed, for instance to become a pathology model.

The terms "in situ" means in the natural or normal place, confined to the site of origin. Accordingly, the use of the feature in situ implies de facto the feature in vivo according to the present invention.

The term "ex vivo" pertains to a biological process or reaction on a target tissue, a body structure taking place outside of the human or animal body, in order to reimplant said tissue or structure on the candidate subject.

By extension, according to the present invention, the term ex vivo refers also to taking out from the body a small fragment from the human or animal body, and taking in vitro a sample of said fragment, or using it as a sample.

According to the present invention, the term "ex vivo" also refers to tissues or body structures, or small fragments of them, removed from humans or animals after death, "post mortem", for subsequent analysis.

The term "molecule" means any chemical, biochemical or biological entity or species that it is desired to retain and therefore detect on a fingerprint. Mention may in particular be made of proteins, peptides, antibodies, hormones, steroids, antigens, in particular derived from infectious agents or from tumor cells, or generated by other pathologic conditions such as degenerative diseases, infectious agents such as bacteria, viruses or parasites, nucleic acids (DNA or RNA), therapeutic molecules, drugs or alternatively antibiotics.

The term "sample" or specimen refers to an elementary collection of biological material existing in or on a target tissue or other body structure.

The quantity of this sample has an order of magnitude consistent with the sensitivity of molecular analysis methods and instruments, such as the TOFI techniques. For example, this quantity is less than $10^{-6}$ g, and preferably less than $10^{15}$ g.

It must be understood that the quantity here above mentioned is a maximum quantity, i.e. no more sample of tissue or body structure is necessary according to the present invention. The sample is taken in a very small quantity. Accordingly, the method of the present invention can be described as non invasive with regard to the method of the prior art. To date, no method or device performing with as little as that has been described.

Furthermore, a device taking a bigger sample than the one covered by the present invention is not adapted since one of the essential characteristics of the present invention is to be as less invasive as possible. Thus devices of the prior art intended to collect more than $10^{-8}$ g are not of interest in the present invention and would not be adapted for the purpose of the present invention.

According to the present invention, this sample is a "raw" sample, which means that only non denaturing and/or non disrupting intermediate treatments may be applied to it, for instance for eliminating impurities, prior to its direct analysis with molecular analysis techniques such as presently used in proteomics.

As here above stated, the samples considered by the present invention are obtained from parts or fragment of biological entities, such as small pieces of tissues, organs, or body structures, for instance withdrawn by mechanical means. Samples can also refer to liquid fractions.

Patterns, spectrum, fingerprints, profiles mean representations according to 2D and 3D axis such as images, graphs, tabular representations, displays, etc. . . . , of the composition (qualitative and possibly quantitative) in a specimen of molecular species or entities. These representations can be stored or supported by data or electronic files, or edited like print outs. Such graphs are obtained after the molecular analysis of the sample, thanks to a specific analytical device, such as a mass spectrometer, fluorometer, or optical detector. The corresponding data are either digital or analogic, and specific algorithms can be used to generate the pattern, spectrum, profile or fingerprint.

The field of "molecular fingerprinting", also called molecular targeting or molecular profiling, in diseases or pathological states, for example cancers, focuses on the detection and/or quantification of appropriate sets of molecules or molecular compositions in order to generate molecular profiles. These molecular profiles can be used as signatures of normal (or reference) biological samples or healthy clinical status versus profiles that exhibit specific modifications in comparison to the normal profile and then feature pathological status. Any kind of molecules can be assayed in order to generate molecular fingerprints. Molecular fingerprinting focuses on the proteins that are active and involved in the development and spread of said disease but also to proteins not directly involved in the pathological process, but can be taken as an indirect signature of the disease without any pathophysiological involvement.

For example, a molecular fingerprinting or protein profiling relates to the determination of the abundance, modification, localization, activity and interaction of proteins in a given body tissue or structure.

The term "lysis" is understood to mean any process which makes it possible to disrupt the membrane or envelope of cells in order to release the biological material of interest, in a complete or partial form, such as proteins and nucleic acids.

DESCRIPTION OF THE INVENTION

1. Method for Determining the Molecular Composition of a Target Tissue or Another Body Structure The method for determining the detailed molecular composition of a target tissue or another body structure of a human or animal body according to the present invention comprises at least two steps.

The first step consists in taking a molecular sample in situ and in vivo or taking a sample ex vivo, of said target tissue or body structure, with the help of an adapted inert sampling instrument.

Two kinds of molecular sampling can occur according to the present invention. The first one is performed in situ and in viva, whereas the second one is performed ex vivo of the candidate subject. The term "candidate subject" refers to a human or an animal for which there is a point in determining the detailed molecular composition or fingerprinting of a target tissue or other body structure.

In some particularly preferred embodiments, the sampling is performed on a human patient, for instance during surgery. In other embodiments, the candidate subject is a non-human animal. In some preferred embodiments, the animal is a female, in other embodiments, the animal is a male. In some embodiments, the candidate subject is suffering from a pathological condition such as a cancer. In some embodiments, the candidate subject is suffering from an infectious disease (due to any type of virus, bacteria, parasites), or a metabolic disease (such as diabetes, obesity, cystic fibrosis). In some embodiments, the candidate subject is suffering from a central nervous system pathology such as a neuro-degenerative pathological condition, the Parkinson's disease, the Huntington's disease or the Alzheimer's disease, epilepsy. Generally, all kinds of neurodegenerative diseases, infectious diseases or metabolic diseases are concerned. Non conventional pathogenic agents, such as prion-caused diseases are also addressed by the invention methods.

It is a further object of this method to use an inert sampling instrument, adapted to take a sample in situ or ex vivo from any kind of tissues or body structures. The features relate to the sampling instrument are mentioned infra.

According to the present invention, the method for determining the molecular composition of a target tissue or body structure minimally perturbs said tissue or body structure. In other words, the method of the invention is less invasive as possible. As the present invention is to be employed either in vivo or ex vivo, this feature is of particular importance. Consequently, according to the present invention, the method minimally injures said tissue or body structure.

According to the present invention, the sample is taken for instance in a maximum quantity of less than $10^{-6}$ g, preferably less than $10^{-15}$ g. $10^{-6}$ g corresponds to a microgram and $10^{-15}$ g corresponds to a femtogram. Indeed, the methods of the present invention minimize the invasive nature of any medical or surgical act having the purpose of collecting data (e.g., biopsies). The sampling instrument is adapted to capture and retain such small quantities. The term "quantity" relates to the property of being measurable in terms of amounts (whether in mass, volumes, or moles). It can be a weight or a volume, depending on the characteristics of the sample. For example, the sample can be taken from a solid tissue or organ. In this situation, the sample can be expressed in weight. It is also possible that the sample be partly fluid. In that case, according to the present invention, the measurement unit chosen can be either grams or liters. As a way of example and in the case of a density of 1, $10^{-15}$ l (i.e., a femtoliter) corresponds to $10^{-15}$ g (i.e., a femtogram).

The sample taken in situ or ex vivo comprises isolated molecules, for instance biomolecules. The term "molecule" means any chemical, biochemical or biological entity of interest that it is desired to retain and therefore detect on a fingerprint. Among the molecules captured by the sampling instrument of the present invention, mention may in particular be made of proteins, peptides, antibodies, hormones, steroids, antigens derived from infectious agents or from tumor cells, infectious agents such as bacteria, viruses or parasites, nucleic acids (DNA or RNA), therapeutic molecules, marker molecules, drugs or alternatively antibiotics. Preferably, the molecules captured by the sampling instrument of the present invention are proteins and more preferably the molecules captured by said instrument are substantially proteins of the extracellular matrix.

The term "isolated" means that the sampled material is removed from its native environment, i.e. in which it is normally found. Thus, an isolated biological sample can be free of cellular components, i.e., components of the cells in which the material is found or produced. An isolated protein may be associated with other proteins or nucleic acids, or both, with which it is associated in the cell, or with protein. But the sample is substantially composed of molecules. However, an isolated organelle or cell may be removed with the molecules of interest from the anatomical site in which it is found in the organism.

The second step of the present method consists in determining the qualitative, and possibly quantitative, molecular composition of said sample, using molecular analysis means having a sensitivity that corresponds with the available quantity of the sample taken in the first step.

The terms "qualitative analysis" relate to the determination of the various entities or species of which a mixture is composed. The term "quantitative" relates to this analysis with regard to quantities or specific numeric values, for these entities or species.

The molecules of interest that are captured by the sampling instrument of the present invention must thus be able to be detected by the molecular current analysis means, according to the present invention. As the sample is taken in a very small quantity, the analysis means must therefore have a high sensitivity.

It is furthermore an object of the present invention to simplify as much as possible the method for determining the composition of a sample.

When it is desirable to determine the protein composition of a sample, several limitations in the analysis of proteins are imposed and then the determination of the proteins in a sample becomes complicated compared to other biomolecules. First, unlike DNA and RNA, proteins cannot currently be amplified. Second, it is often difficult to purify proteins from a sample for separate analysis. Third, there are few solvents in which all proteins are soluble and which are compatible with protein analysis techniques. However, the largest obstacle to an analysis of the proteins present in a sample is often the large number that can be present. Accordingly, an accurate analytical technique has to be used in order to determine the presence of proteins in the sample.

As a way of example, it is not possible according to the present invention to perform a SDS-polyacrylamide gel electrophoresis to analyse the complex protein mixtures in a biological sample according to the present invention, because of the poor sensitivity level of the presently available techniques.

Mass fingerprinting is one of the molecular analysis means having a sensitivity that is compatible with the quantity of the sample taken in the first step that can be used according to the present invention. Typically, a sample is ionized and a mass spectrum of the ionized sample molecules is obtained by mass spectrometry. Even if the molecule quantity captured and retained on the sampling instrument is in the femtogram range, the sample may still contain millions of molecules. The presence of the molecules in the sample is represented by a molecular spectrum (i.e. profile). The presence of a particular molecule can be further determined by correlating the information contained in the sample mass spectrum with known or theoretical mass spectra for the molecule. According to the present invention, it is thus possible to use mass spectrometry to develop profiles of proteins active in samples taken in a quantity in the femtogram range.

Various molecular analysis methods can be used according to the present invention. The techniques hereunder listed are not limitative. All these techniques presently enable resolving complex mixtures of several hundred of thousands to several millions of molecules.

Although mass spectrometry is one the preferred molecular analysis method described here, several other different techniques can be used to address the problem of the detection and/or quantification of the samples collected to the present invention.

The skilled person will find various available techniques that are appropriate to get sensitive and accurate data to generate profiles or fingerprints that are required for the final biological sample analysis according to the invention.

For example and without limitation molecular analysis can be carried out by fluorescent detection or sensitive mass nano detector; or based on physical principles such as surface plasmonic resonance (based on the detection of the "evanescent wave" as it is the case with an apparatus sold by the Biacore company); or based on electrical or electronical signal detections generated by or related to the binding of the samples to the sampling instrument; or by detection of any biological interactions between probe molecules immobilized on the retaining surface of the sampling instrument.

The invention method can be extemporaneously performed. The term "extemporaneous" means: as soon as the sampling is obtained, without delay. In the present invention, the term "extemporaneous" is not intended to mean without treatment, as found sometimes in the literature.

The integration of the invention method to a surgical or diagnostic procedure provide a true extemporaneous procedure inaccessible to date for molecular analysis. Extemporaneous means fast, integrated in the current medical procedure with a diagnostic response not delaying the medical procedure waiting for the adequate response.

Possibly, the method according to the present invention comprise an intermediate step, which consists in treating the sample captured and retained on said sampling instrument.

According to an embodiment of the present invention, the treatment of the sample excludes the use of any disruption or lysis method. As mentioned below, this restrictive feature brings advantages.

Alternatively, said intermediate step may comprise a proteolyse of the proteins contained in said sample, so as to submit the resulting peptides to mass spectrometry, or any chemical modification appropriate for the subsequent detection It is well known that in order to characterize specific molecules in a complex mixture, the molecules of interest must be completely soluble. Different treatments and conditions exist to solubilize different types of molecule samples.

For example, proteome analysis, which is "the analysis of the protein complement expressed by a genome", involves the separation, identification, and quantification of many proteins simultaneously from a single sample.

As some proteins are naturally found in complexes with membranes, nucleic acids, or other proteins, some proteins form various non-specific aggregates, and some proteins precipitate when removed from their normal environment. Thus prior art methods require numerous, complicated and time-consuming solubilization methods. Furthermore, the effectiveness of solubilization depends on the choice of the cell disruption method, protein concentration and dissolution method, choice of detergents, and composition of the sample solution. If any of these steps is not optimized for a particular sample, separations may be incomplete or distorted and composition information may be lost.

Methods for analyzing intracellular proteins, in which the cells from solid tissue, or other biological material, must be effectively disrupted, have been developed.

It is generally considered that any appropriate sample preparation involves a step of lysing. Lysis methods (e.g., disrupting methods) have long been used in laboratories in order to disrupt cells and release intracellular molecules. A great number of biologists is persuaded that the disruption methods are absolutely essential in order to solubilize molecules from a sample and then determine their composition.

According to one embodiment of the present invention, the sample of the target tissue or other body structure, retained on the active surface of the inert sampling instrument, is not subjected to any disrupting methods. A prejudice in the art, i.e. a widely held opinion of a technical fact, has been overcome. See INTRODUCTION A LA BIOLOGIE MOLECULAIRE DE LA CELLULE (Médecine-Sciences Flammarion Ed., 1999); refer for instance to page 160.

Different kinds of disruption methods exit. In one embodiment of the present invention, all these disruption methods are excluded from the method for determining the detailed composition of the target tissue or other body structure according to the present invention. The disruption methods are generally classified in gentle lysis methods and vigorous gentle methods.

There are several gentle lysis methods, and in particular:
osmotic lysis which requires to suspend cells in a hypoosmotic solution;
freeze-thaw lysis which requires one or more cycles of rapid freezing of cell suspension, using liquid nitrogen for cooling, then thawing for example at room temperature;
detergent lysis in which detergents solubilize cellularor subcellular organites, membranes, lysing cells and liberating their contents.

More-vigorous lysis methods are employed when cells are less easily disrupted, i.e. for cells in solid tissues or cells with tough cell walls. By way of example, they can be:
a mechanical homogenization based on grinding with a mortar and pestle; or using, for example, handheld devices, such as Dounce or Potter-Elvehjem homogenizers, blenders or other motorized devices, which subject the biological sample to an alternating movement, of variable amplitude and/or frequency, or to a rotating movement of the vortex type; or based on glass bead homogenization in which the abrasive action of the vortexed beads break cell walls, freeing the cellular content;
a French pressure cell (or any equivalent device) with which cells are lysed by shearing forces resulting from forcing cell suspension through a small orifice under high pressure;
a sonication which requires ultrasonic waves generated by a sonicator and lyses cells through shearing forces;

The use of these methods often requires the addition of additional reagents such as, for example, enzymes and/or detergents. As proteases may be liberated upon cell disruption, the protein sample is generally protected from proteolysis using one or several protease inhibitors. Examples of protease inhibitors are PMSF (Phenylmethylsulphonyl fluoride), benzamidine, Amastatin, E-64, Antipain, Elastatinal, Leupeptin, Bestatin, Pepstatin, 1,10-Phenanthroline, Chymostatin, Phosphoramidon, 3,4-dichloroisocoumarin, TPCK (Tosyl Phenylalanyl ChloromethylKetone), DFP (Di-isopropylfluorophosphate), TLCK (Tosyl Lysyl ChloromethylKetone).

Sometimes the above-mentioned techniques are combined (e.g. osmotic lysis following enzymatic treatment, freeze-thaw in the presence of detergent). Furthermore, several commercial kits are available for the rapid extraction of proteins from cells. These kits generally employ the use of a detergent solution to disrupt the cell membrane, thereby releasing the cellular components including protein.

According to the one embodiment of the present invention, none of the above disruption methods is used, either mechanical or chemical. Protease inhibitors are not necessarily required.

According to the method for determining the composition of the sample of the present invention, possibly in an intermediate step, i.e. between the first and second here above defined steps, the sample captured and retained on said sampling instrument is treated. However the use of any lysis or disruption prior art method as mentioned supra is excluded during such an intermediate step.

Such treatments are only intended for preparing the sample to the second step, for instance purifying it.

It is thus another object of the present invention to provide a method for determining the detailed molecular composition of a target tissue or another body structure of a human or animal body, which possibly comprises the step of treating the sample captured and retained on said sampling instrument, said treatment excluding the use of any disruption or lysis methods.

2. Method for Molecular Fingerprinting a Target Tissue or Another Body Structure Two kinds of molecular fingerprinting can be performed according to the present invention. The first one is performed in situ and in vivo, whereas the second one is performed ex vivo.

The method for molecular fingerprinting a target tissue or another body structure of a human or animal body (for example patient's body) comprises several steps.

The first step consists in providing an adapted sampling instrument comprising a retaining surface, as mentioned below.

The second step consists in positioning said instrument at the location of the target molecular fingerprint, for example within or outside said human or animal body, or inside the target tissue or body structure or at the surface thereof.

Then, the third step consists in contacting said retaining surface of said instrument for a determined period of time with said target tissue or body structure. For example, the contact lasts at least 60 seconds, or preferably less than 10 seconds.

During this contact period, the molecular components of the sample, for instance proteins, are absorbed, interact or bind to the retaining surface. This binding can be enhanced or favored by imposing a limited electric field between the sampling instrument and a convenient electrode.

Finally, the contact of said retaining surface with said target tissue or other body structure is stopped.

In one embodiment, as above-mentioned, the method for molecular fingerprinting is performed in situ and in vivo. In that case, the method comprises the steps of:
a) providing an adapted sampling apparatus comprising a retaining surface;
b) positioning said apparatus within said human or animal body;
c) contacting said retaining surface of said apparatus for a determined period of time with said target tissue or body structure; and
d) removing said apparatus from the human or animal body, with the retaining surface out of contact of said body.

In another embodiment, the method for molecular fingerprinting is performed ex vivo. In that case the molecular fingerprinting is obtained by the method comprising the steps of:
a) providing an adapted sampling instrument comprising a retaining surface;
b) positioning said instrument inside the target tissue or body structure or at the surface thereof; and/or
c) contacting said retaining surface of said instrument for a determined period of time with said target tissue or body structure, or a fragment thereof;
d) suppressing the contact with said target tissue or other body structure, or said fragment.

Preferably, the sampling instrument comprises an opening/closing device. Such a device insures that sampling is made at a precise level of a targeted tissue or body structure.

Accordingly, the method for obtaining an in situ molecular fingerprint of a target tissue or body structure of the present invention comprises the steps of:
a) providing an adapted sampling instrument comprising a retaining surface;
b) positioning said instrument in closed position in adjacency to said target tissue or body structure;
c) opening said instrument for a determined period of time, so that the retaining surface contacts said target tissue or body structure;
d) closing said instrument; and
e) removing said instrument from the human or animal body.

In one embodiment the positioning of said sampling instrument is preferably three-dimensionally spotted using positioning software. In this case, a mapping system for examining the target tissue or other body structure within a human or animal body while recording and determining an anatomical location of the molecular fingerprint is provided.

Such systems are currently available for surgery, in particular micro-surgery and can be used in conjunction with a sampling instrument as previously described.

Such a system includes for instance a substantially hard, suturable, tackable support, and means for a graphic representation of the target tissue or other body structure anatomy. For example, the graphic representation displays the cerebral convolutions, and an alpha-numeric background grid to define the location of the molecular fingerprint on the map system. Using such a system permits to increase precision of the location of the sampling site, resulting in increased accuracy and precision of the fingerprint.

If necessary, the method for in situ molecular fingerprinting the tissue or body structure further comprises a stereotactic surgical technique.

If necessary, the methods of the invention further employ appropriate endoscopic apparatuses. The skilled person is aware about such apparatuses which can be used with a sampling instrument as previously described. As a way of example, such endoscopic apparatus are well known in the following medical arts: Ear, Nose and Throat (ENT), digestive, pneumology, urogenital, intracerebral cavities, vascular (e.g. heart, vessels) examination and surgery.

Thus some of the apparatus considered by the invention are endoscopic apparatus so as to allow the investigation of the following body structures: oral cavity, digest tract, uro-genital tracts, intracerebral domains, vessels, heart. Such an apparatus can embark a sampling instrument a protected retaining surface that can be remotely controlled (for example by external magnetic stimulation) when the instrument has reached the adequate location at the target level of the body structure, so as to promote the opening of a door protecting the retaining surface, making it unveiled and exposed to the outside medium and available for biological sample fingerprinting in close contact with the body structure of interest.

In accordance with one embodiment of the present invention, as already explained above, the molecular fingerprint so obtained is neither lysed nor disrupted. In this case, the molecular fingerprint is neither contacted with a lysis matrix nor with a composition or compound which causes or aids in cell lysis or disruption. No mechanical or physical forces (e.g., pressure, sonication, temperature (heating, freezing), and/or freeze-thawing etc.) are used in accordance with the invention. Any combination of mechanical forces, physical forces or lysis compositions/compounds is neither used to disrupt/lyse the molecular fingerprint.

3. Method of Diagnosis or Prognosis

Methods of diagnosis typically rely upon a huge number of measurements and observations to determine the presence and nature of a disease. Clinicians look for "deviations from the norm", especially changes that have a qualitative and/or quantitative relationship with a known set of symptoms characterizing a particular disease. In addition to the physical symptoms, diseases cause changes in the chemical composition of the tissues or other body structures, for example organs, they affect; these differences are the basis of everyday diagnostic methods (chemical tests, medical imaging techniques and anatomoclinical method). Generally, it is difficult for practicians and physicians to directly and rapidly make decisions about treatment of a pathological state or of a stage in the development of a disease, using physical symptoms and typical diagnostic methods as above-mentioned because all the prior art methods are time-consuming, require a number of assistants and sophisticated analysis techniques.

It is thus desirable to provide a method for rapidly and easily diagnosing a disease or grade in the development of the disease. The diagnostic method according to the present invention provides all the just above-mentioned features. Indeed, the determination of the detailed molecular composition of a target tissue or other body structure, for example the brain or a tumor, with the help of a molecular fingerprint of said tissue or structure, can be used to reveal and classify the pathological states, in particular with regard to the non pathological ones, and also to classify the stages in the development of a disease, for example a tumor. This classification can thus be used to make decisions about treatment. It can also be used to predict the occurrence and development of a given disease or pathological state, and then prevent the same instead of curing it.

Of course, not only the molecular fingerprint of the tumor can be used to allow the discovery of a new pathological state but can also be of major interest to assess and monitor the progression of disease, for example during the time of treatment.

Molecular fingerprints will be also useful for enabling clinicians to provide patients with a serious information about their state or with a complete diagram of how the disease is expected to behave, and also take samples of normal tissue and sample of different grades to follow the development of a disease correlated with a tissue or body structure.

It is a possible way to screen patients for the first signs of the disease, for example cognitive impairment, and get early information for accurate diagnostic soon after development of the pathological state. For example patients with a particular disease, for example Parkinson's disease or any cognitive disorder, may have distinct protein patterns in a particular area of the brain, setting them apart form patients with pathologies not related to the standard Parkinson's disease.

A method for diagnosis or prognosis of a pathological state or a stage in the development of a disease of a human or an animal, said pathological state or development stage being correlated with a tissue or other body structure, comprises the steps of:

a) taking a sample in situ and in vivo or taking a sample ex vivo, of said target tissue or body structure, for example in a quantity of less than $10^{-6}$ g, for example less than $10^{-15}$ g, with the help of an adapted sampling instrument;

b) possibly treating the sample captured and retained on said sampling instrument, c) extemporaneously determining the quantitative and/or qualitative molecular composition of said sample, using molecular analysis means having a sensitivity that corresponds to the quantity of the sample taken in step (a);

d) comparing the molecular composition obtained in step c) with either the molecular composition obtained from a comparable tissue or body structure of a human or an animal in a non pathological state, or with the molecular composition obtained from a comparable tissue or body structure of a human or an animal non developing the disease.

Preferably, said molecular composition is represented in the form of a pattern/profile/spectrum.

According to one embodiment of the present invention, the treatment of the sample in step b) is non denaturing and/or non disrupting.

The above diagnostic method practised on the human or the animal body is carried out by a practitioner in the fields of human or veterinary medicine respectively.

The above-mentioned steps (a), (b) and (c) all belong to the more general method step which can be called collection of data. The diagnostic method of the present invention furthermore comprises the comparison of these data with standard values, i.e. the method step (d) here above. Making a diagnostic also requires the finding of a significant deviation during the comparison with standard values and the attribution of the deviation to a clinical picture.

The attribution of the deviation to a clinical picture according to the present invention is either an intellectual exercise or either reached by means of the analysis means comprised in the analysis chain of the present invention.

According to the present invention it is possible that some of the method steps of technical nature are carried out by a device without implying any interaction with the human or animal body, for example by means of a software or protein microarray.

4. Sampling Instrument for Taking a Sample of a Target Tissue or Another Body Structure According to the present invention there is provided a sampling instrument for determining the molecular composition of a target tissue or another body structure, at a determined location (e.g. predetermined location).

Such an instrument will be described with reference to FIGS. 1 to 6.

Because the instrument is in contact with the sampling site, the properties of the instrument become important.

Said sampling instrument is inert. It is made of any materials or composite assembly of different parts or materials. Any kind of material can be used, such as metal, glass, plastic, polymer, natural components, ceramics, silicium, provided that said materials are not proved to elicit adverse biological reactions, such as in the patient's body.

According to the present invention, the sampling instrument is adapted for taking a sample in situ and in vivo or taking a sample ex vivo of a target tissue or body structure, for example in a quantity of less than $10^{-6}$ g, for example of less than $10^{-15}$ g. As explained before, the term "quantity" here means maximum quantity. Indeed it is an object of the present invention to be as less invasive as possible. The sampling instrument is in particular adapted to molecular fingerprinting the target tissue or other body structure, i.e. for taking fingerprints on the molecules, preferably proteins that are available at the target location in or on the target tissue or body structure. The sampling instrument is adapted to take a trace, i.e. a very small amount, usually one quantitatively assessable with current biological techniques for assays of molecular components.

As mentioned supra, two kinds of sampling can be made according to the present invention. The first one is performed in situ and in vivo, whereas the second one is performed ex vivo, in the here above defined acceptation of this term. The term "adapted" directly depends on the type of molecular fingerprint. In other words, the sampling apparatus is either adapted for in situ and in vivo molecular fingerprinting the target tissue or other body structure, or adapted for ex vivo molecular fingerprinting the target tissue or other body structure.

The sampling instrument for the molecular fingerprinting according to the present invention is adapted primarily for access to the tissues and organs of the living human or animal body.

The sampling instrument of the present invention may assume a wide variety of configurations, designs or constructions. According to a preferred embodiment of the present invention, for internal in vivo sampling, it comprises an elongated active member with a distal operative end and a proximal end, and said distal operative end comprises a retaining surface. This retaining surface is intended and arranged to be in contact with said tissue or body structure, and capture the molecules required for the subsequent molecular analysis.

For example, the instrument (e.g. a probe or a catheter) can be flexible, rigid, curved, steerable, small, light, disposable, sterilizable, etc. . . .

In another embodiment, where the sampling instrument is embarked, no manipulating device is necessary, and an exogenous remote manipulation, using for example electric or magnetic stimulation means, is implemented.

In one embodiment of the present invention, the sampling instrument, and in particular the elongated active member, have a handle or other manipulating means at the proximal end, in order to permit the operator, for example the surgeon, to manipulate the instrument, in particular the elongated active member, from one end of the instrument, and in particular of the elongated active member.

In one embodiment of the present invention, the sample (or molecular fingerprint) is taken in situ and in vivo. In that case, the primary purpose of the instrument is to introduce or affix the retaining surface into or onto the animal or human body in an open or endoscopic procedure and to permit the operator, in particular the surgeon, to manipulate the instrument from one end. It is preferred in that embodiment that the instrument be flexible and/or curved and/or steerable so as to allow the manipulator to move the instrument into at least close proximity of the tissue, organ or body structure to sample (or fingerprint). This small, flexible or rigid, adapted sampling instrument may be inserted into various parts of the body, in a manner very similar to electrodes.

Retaining Surface

The term "retaining surface" means any material/substrate/absorbent having an active surface that binds molecules, in particular bio molecules. According to the present invention, the active surface is arranged to preferably bind proteins. The retaining surface of the present invention may be compared with a "blotting paper".

The retaining surfaces useful in this invention are substrates/absorbents/materials which facilitate the direct or indirect attachment of molecules thereto and minimally interfere with the thus captured and retained molecules. The retaining surface has further to minimally interfere with the subsequent detection of the captured and retained molecules.

The retaining surface must have attachment/binding/attraction characteristics. In other words, the molecules of interest have to be hold by a physical and/or chemical force or agent of any kind. The binding means can derive from chemical or biological molecular recognition. Among the binding agents that can attach to the retaining surface of the invention, mention can be made to any chemical, biochemical or biological entity. In particular, mention can be made to proteins, peptides, hormones, steroids, antigens derived from tumor cells, viruses, nucleic acids (DNA or RNA).

Preferably, any retaining surface according to the present invention maximally facilitates the capture, attachment and retention of proteins thereto. Proteins are composed of linear, unbranched, chains of amino acids. The structural and functional properties of the protein derive from their linear sequence of amino acids. In particular, the physicochemical interactions between these amino acids determine the structure of the folded protein. These kinds of interactions are reproduced according to the invention on the retaining surface. Thus, the retaining surface preferably has attachment/binding/attraction characteristics similar from those existing in proteins.

The interactions arranged on the retaining surface can be covalent and non-covalent. There are several covalent and non-covalent interactions, for example:

electrostatic interactions, such as ionic charge interactions, particularly positive or negative ionic charge interactions, like between amino acid side chains that carry an electrostatic charge at a physiological pH (for example, aspartic acid and glutamic acid, on the one hand, and arginine, lysine and histidine on the other hand);

van der Weals interactions;

hydrogen bonds, i.e. the partial sharing of a hydrogen atom between two electronegative atoms (for example, hydrogen from the hydroxyl function of amino acids like serine and threonine or hydrogen from the amide function of amino acids like asparagine and glutamine);

hydrophobic or hydrophilic interactions, i.e. interactions between non-polar or polar molecules (for example, alanine, valine, leucine and isoleucine, or tryptophan and phenylalanine) or between methionine;

reversible or non-reversible covalent interactions (for example, covalent interaction is seen in the disulfide bond formed between cysteines);

immobilized dye interactions;

charge transfer interactions;

coordinate covalent bonds with a metal ion on the retaining suface;

enzyme-active site binding;

biospecific interactions, such as ligand (for instance antigen/antibody) interactions, interations with aptamers, receptors.

Combinations of two or more of the foregoing bindings are also possible.

Examples of substrates/absorbents/materials according to the present invention thus include all kinds of material upon which biological molecules, in particular proteins are directly or indirectly embeddable/attachable.

These substrates can be chosen so as to directly attach the target molecules, due to the existence in the chemical structure of the substrate of chemical groups, such polar substituents. These substrates can also be treated so as to coat the retaining surface with attaching means, such as "probe" entities, capable of linking with the target molecules in the sample.

Target molecules may be labelled, for instance on the retaining surface, prior to their molecular analysis.

In some embodiments, substrates/absorbents/materials comprise a ferromagnetic metal. In some embodiments, this metal is coated with a non-soluble polymer material.

In some embodiments, substrates/absorbents/materials are made of a polymer. In that case, the active or retaining surface can be produced by coating or synthesizing polymers thereon. According to one embodiment, the polymer can have, coated on its surface, other materials, for example chemical compounds for adjuvants for modifying surface properties, such as surfactants.

In one embodiment, the retaining surface is made of different kinds of substrates/absorbents/materials.

The retaining surface according to the present invention can have different sizes and shapes. However, the retaining surface has to be adapted to the elongated active member to which it is attached, and also to the target tissue or body structure from which the sample is to be taken. According to the present invention, most preferably, the sampling instrument and method are micro invasive and non traumatizing.

In an alternate embodiment, the retaining surface is divided into quadrangles, and possibly each quadrangle has a different substrate/absorbent/material.

Preferably, all of the substrate/absorbent/materials in all quadrangles are substantially similar, or respectively different. In some embodiments, each quadrangle has more than one substrate/absorbent/material. The retaining surface of the present invention can have varying number of quadrangles, or distinct sub-areas.

The retaining surface preferably can include from about 2 to about 10,000 or more quadrangles, or elementary arrayed spots, or "pixels".

Each quadrangle preferably has an elementary surface area of 1 $mm^2$ or less, for example 0.1 $mm^2$ or 0.01 $mm^2$. The number of spots per $cm^2$ or $mm^2$ of retaining surface area can vary according to the used spotting techniques.

The retaining surface may be made of microarrays, that is to say sets of miniaturized elementary spots.

In a preferred embodiment, the retaining surface is planar, and contains protein chips, also called protein microarrays. The protein chips are generally powerful tools.

As thousands of molecules can be screened simultaneously using this technology, protein chips may be used to improve timeliness, effectiveness, accuracy and overall benefit-to-cost ratio of the invention method in two respects:
  first, these protein chips can be used to directly sample the target tissue or organ,
  second, these protein chips with the sample on it can be used directly, possibly after an intermediate treatment as hereabove defined, so as to proceed to the molecular analysis.

The basic construction of such protein chips has some similarities to DNA chips, such as the use of a glass, silica, or plastic surface dotted with an array of retaining sites. Capturing molecules such as DNA or antibodies that are designed to capture proteins can be spotted in or on these sites. In the present invention, these capturing molecules are designed for facilitating the attachment of proteins thereto and minimally interfering with the captured and retained proteins. Various well known surface chemistries enable the immobilization of defined quantities of said capturing molecules on each spot. In the present invention, the protein chip does not have to present an ability to capture and retain a big quantity of proteins.

With markers or other methods of detection revealing the spots that have captured the target proteins, protein microarrays are very attractive components or tools for performing the present invention.

For instance, the protein microarrays are those made by Ciphergen Biosystem Inc.

Other biochip devices may be used. For example:
  LabChip Technology (Caliper Technologies Corp.);
  Trinectin Proteome Chip (Phylos Inc.);
  Tissue Microarray Technology;
  According to the present invention, disposal chips can also be used.

Protein microarrays are affixed for instance to the distal operative end of the active member of the sampling instrument. In that case, having contacted the protein chip with the target tissue or body structure, the protein micro-array can be detached from said distal operative end, and subsequently and possibly and directly submitted to molecular analysis.

In one embodiment, the protein micro-array can be produced by arraying capturing proteins on glass slides. Then the protein microarray is possibly affixed to the distal operative end of the active member of the sampling instrument. In another embodiment, the protein micro-array can be produced by arraying capturing proteins directly on the distal operative end, so as to produce the retaining surface.

Once contacted with the retaining surface, some molecules or target tissue or organ selectively form pairs by binding with same sites of the substrate/absorbent/material. For example, a "probe molecule" on the biochip captures a "target molecule" of the tissue or body structure. The molecules that do not form pairs are not retained at the retaining surface. Where the pairs are formed at the retaining surface, they can be visualized if required by labelling said target molecules on the substrate/absorbent/material.

A sampling instrument 1, for instance made of a metal, according to the present invention is shown by FIGS. 1 to 6.

It comprises an elongated active member 10 with a proximal end 3 and a distal operative end 2. The distal operative end 2 has a retaining surface 12 made of a plurality of elementary retaining surfaces 121, 122, 123, 124, 125 (refer to FIG. 2 or 3), arranged as previously described for contacting directly said target tissue or body structure, capturing and retaining molecules of said target tissue or body structure thereto.

According to FIGS. 1 to 4, the retaining surface 12 is made of 5 elementary retaining surfaces (121, 122, 123, 124, 125). Theses figure illustrate the present invention but they do not limit the scope of the present invention. Accordingly, the retaining surface can comprise a single elementary surface, or at least two elementary surfaces. There is no maximum number of elementary surfaces.

As not shown, the sampling instrument 1 further comprises manipulating means at its proximal end 3, in particular of the active member 10.

Figure 4:
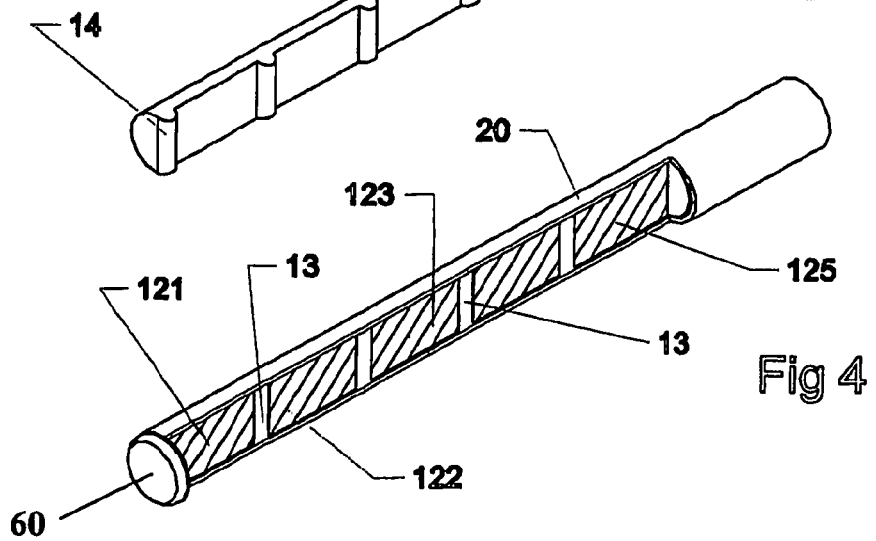
FIG. 4 is a perspective view of the active member of the sampling instrument shown on FIG. 1, for in situ molecular fingerprinting a target tissue or other body structure.
Figure 7:
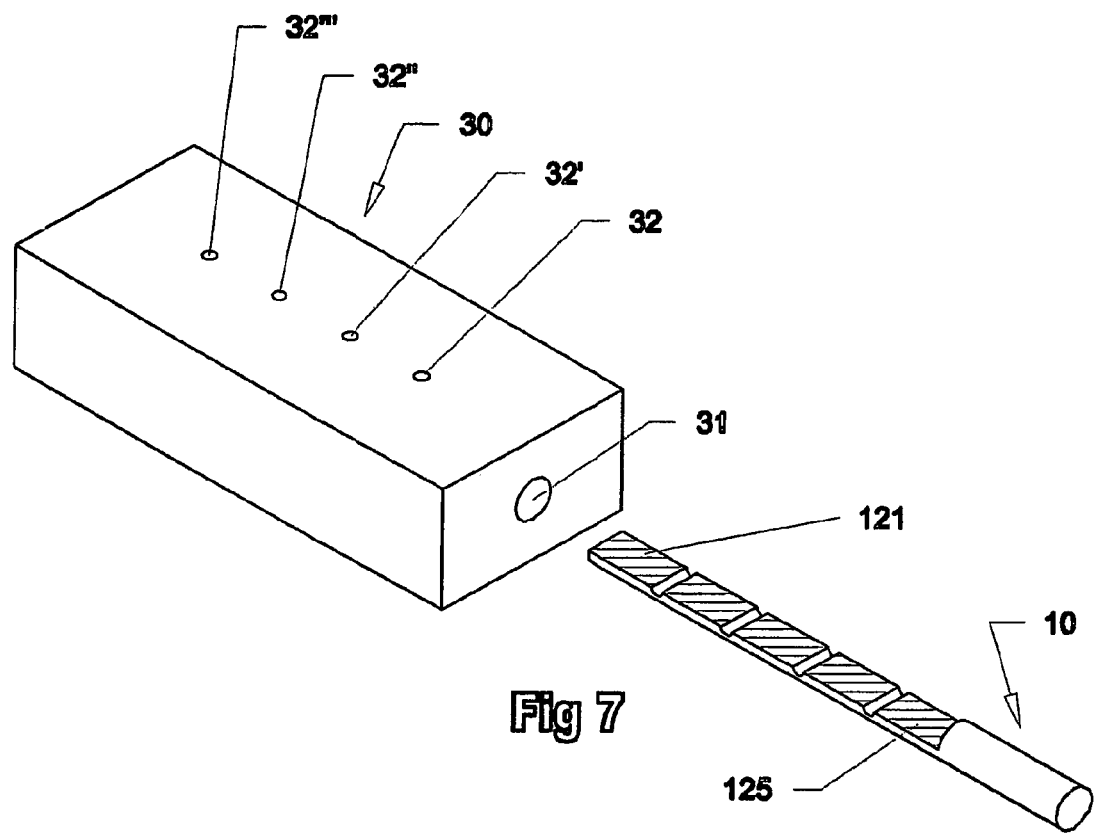
FIG. 7 schematically illustrates a sampling apparatus according to the present invention comprising a sampling instrument and removing means.
Figure 8:
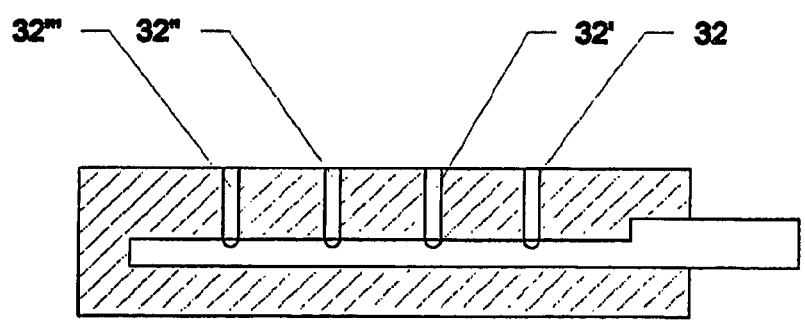
FIG. 8 is a vertical section view of the active member positioned within the removing means.
Figure 9:
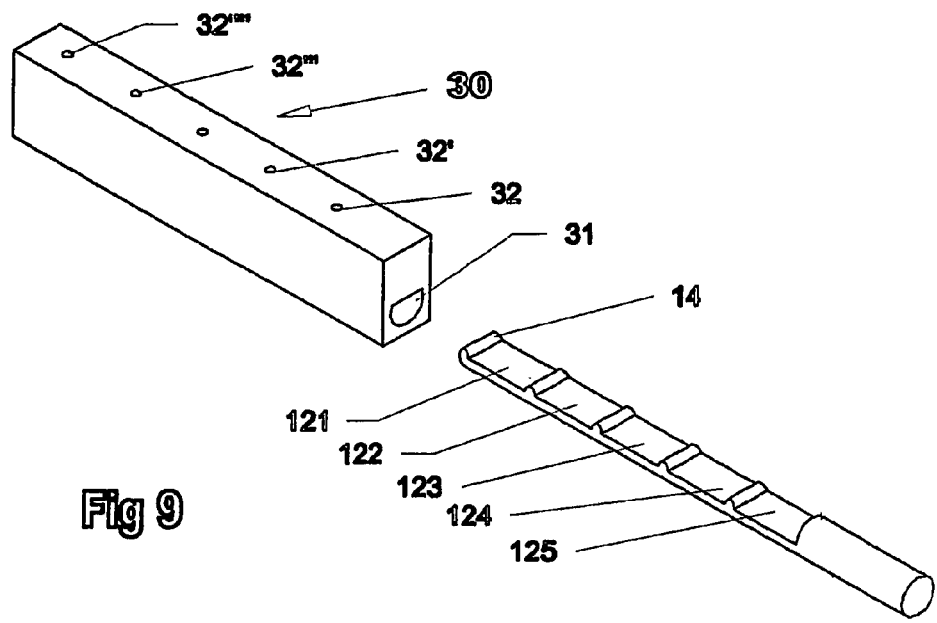
FIG. 9 schematically illustrates another sampling apparatus according to the present invention.

The instrument of the present invention further comprises a hollow tubular body 20 having:
  a larger diameter than said elongated active member 10, so as to movably receive said member; said active member is movable in translation along the body 20 and around its axis;
  stop means 60 intended to stop the active member within said hollow tubular body 20, so as to position the retaining surface 12 correctly with regard to the two relative positions hereunder described (refer to FIG. 4).

The elongated hollow component 20 comprises a distal aperture 31, which is closed by the back side 10a of the active member 10, in a first angular position of said member relative to said component (refer to FIG. 6), and which is open in a second angular position of said member relative to said component, (refer to FIG. 5) said open position exhibiting the retaining surface 12 of the active member 10.

Figure 2:
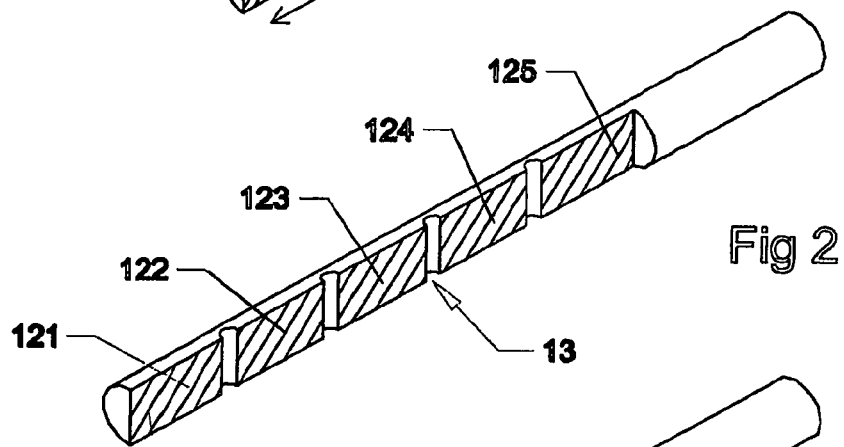
FIG. 2 details the distal operative end of the active member of the sampling instrument shown on FIG. 1.
Figure 3:
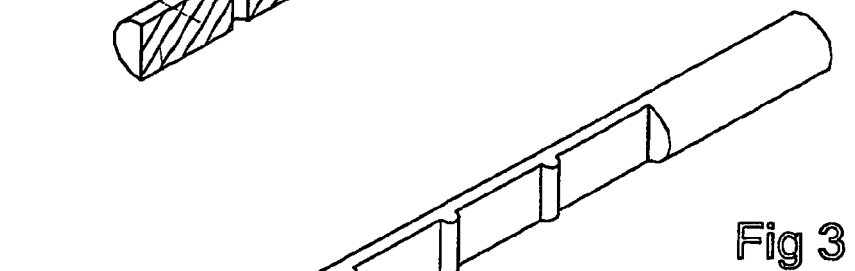
FIG. 3 details the distal operative end of a further embodiment of the invention.

The retaining surface 12 comprises at least two elementary surfaces 121, 122 separated by a groove 13, as shown by FIG. 2, or by a rib 14 as shown by FIG. 3.

The sampling instrument body is preferentially formed out of metal or a thermoplastic, such as a polycarbonate or a polyurethane. However, many other materials will be obvious to those skilled in the art.

With a sampling instrument as previously described, it is thus possible to collect in situ or ex vivo on the retaining surface 12 untreated isolated biological material, i.e. native molecules, comprising in particular proteins.

The term "isolated" means that the biological material is removed from the environment in which it is normally found. Thus, an isolated biological material can be free of cellular components, i.e., components of the cells in which the biological material is collected. An isolated protein may be however associated with other proteins or nucleic acids, or both, with which it associates in the cell, or with cellular membranes if it is a membrane-associated protein. The sample is thus substantially composed of molecules. However, isolated organelles or cells may be removed from the anatomical site in which the biological material is collected.

The meaning of "untreated" refers to material that has been isolated under conditions that reduce or eliminate the presence of unrelated materials. According to the present invention this unrelated material including native materials from which the material is obtained, is present on the retaining surface. For example, the biological material is not substantially free of nucleic acids with which proteins are associated in a cell. The term "substantially free" is operationally used, in the context of analytical testing of the material.

According to the present invention, the biological material which is retained by the active surface is crude or native, which is advantageous compared to prior art (see examples).

The size of the sampling instrument of the present invention is adapted for taking a sample without traumatizing the tissue of body structure, for example brain. Therefore, the length of the sampling instrument varies according to the site of tissue or body structure to be sampled. As an example, the length of the sampling instrument, i.e. the elongated active member and hollow tubular body, is at least 100 mm, for example 150 mm or 200 mm.

The diameter of the sampling instrument is as small as possible, for example lower than 5 mm, preferably lower than 4 mm, and more preferably lower than 3 mm. As an example, the external diameter of the sampling instrument is 2 mm for taking a sample into the brain.

The hollow tubular body has a larger diameter than the elongated active member, so as to receive the elongated active member. Accordingly, as an example, the hollow tubular body has an external diameter of 2 mm and the elongated active member has an external diameter of 2 mm minus epsilon, for example 1.9 mm.

The retaining surface may be 10 mm in length. As an example, the retaining surface is made of 5 elementary retaining surfaces of 1.9 mm in length. As another example, the retaining surface is made of 20 elementary retaining surfaces of less than 1 mm in length.

5. Apparatus Comprising a Sampling Instrument

According to the present invention, there is also provided an apparatus which comprises the above-mentioned sampling instrument.

As shown by FIGS. 7 to 11, the apparatus may further comprise removing means, intended to separate and recover the sample retained at the retaining surface of the active member.

The removing means can comprise a source of liquid medium and additional means 30 for contacting said liquid medium with the sample taken in situ and in vivo, or taken ex vivo, from a target tissue or another body structure for instance, in a quantity of less than $10^{-6}$, and retained on the retaining surface 12 of the active member 10 of the sampling instrument 1.

Said removing means may be distinct from the instrument and complement it, as shown by FIGS. 7 to 11.

In an alternate embodiment, they may be part of the instrument 1. In that case, they may be situated at the surface of the instrument, or within said instrument. Possibly, the active member 10 of the instrument has two positions relative to said elongated component 20, i.e.:

a first position in which said sample is captured and retained on said retaining surface 12, and a second position in which said retained sample is contacted with said liquid medium.

Referring to FIGS. 7 to 11, an apparatus constructed according to a preferred embodiment of the present invention is shown. As shown, removing means 30 are distinct from the sampling instrument 1. Removing means 30 comprise an aperture 31 adapted to receive the distal operative end of the active member 10. Washing chambers 33, 33', 33'', 33''', 33'''' are closed when said retaining surface 12 is positioned inside said chamber. Five apertures 32, 32', 32'', 32''', 32'''' permit to introduce and remove the liquid medium respectively in the washing chambers 33, 33', 33'', 33''', 33''''.

Preferably the number of apertures for introducing and removing the liquid medium in the washing chambers is the same that the number of washing chambers.

Figure 10:
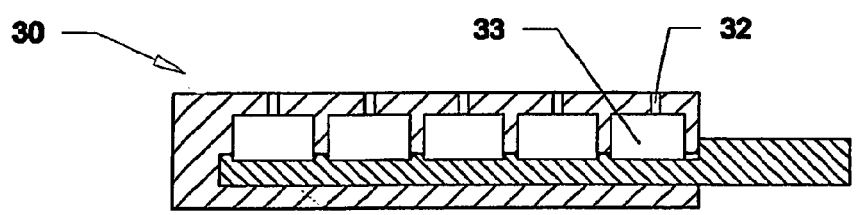
FIG. 10 is a vertical section view of the active member positioned within removing means.
Figure 11:
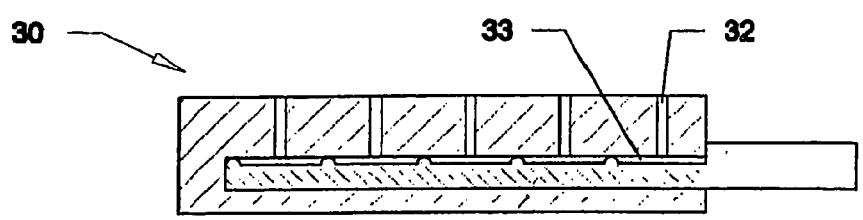
FIG. 11 is another vertical section view of the active member positioned within removing means according to a further embodiment.

As shown in FIG. 10 and FIG. 11, the volume of the washing chamber 33 can vary.

According to one embodiment (not shown in the drawing), the apparatus comprises positioning means for positioning the sampling instrument 1 within said target tissue or body structure. The positioning of said sampling instrument is preferably three-dimensionally spotted, using for instance a stereotactic location software. In this case, there is provided a mapping system for examining the target tissue or other body structure within a human or animal body, while determining an anatomical location of the target tissue or other body structure from which the sample is taken. Such an apparatus includes a means for a graphic spotted representation of the target tissue or other body structure anatomy. For example, the graphic representation illustrates the cerebral convolutions, and an alpha-numeric background grid to define the location of the sample on the mapping system. Such positioning means increase precision of the location of the sampling site resulting in increased accuracy and precision.

If necessary, the apparatus of the invention is an appropriate endoscopic apparatus including a sample instrument as previously described endoscopic apparatuses are well known for viewing the internal region of a body not otherwise viewable. Such viewing is accomplished by introducing into the body an endoscope capable of optically communicating visual information regarding the interior of the body to a viewer or to video imaging equipment. The endoscope typically is a long, slender body with an image capturing portion at the distal end and a handle or other manipulating means at the proximal end. The endoscope may include various lenses, a fiber optic cable light source, and a camera. The video imaging equipment includes various video processing devices, a video monitor and/or video recorder which is capable of presenting video information received from the endoscope to a viewer. Thus, a video record of a relatively inaccessible region of the body could be viewed live or from recorded tape.

According to the invention, a sampling instrument makes part of a video apparatus as previously described.

According to one embodiment (not shown in the drawing), the apparatus of the present invention comprises fixing means for fixing the target tissue or body structure to be sampled and positioning means for positioning the sampling instrument within said target tissue or body structure, with reference to said positioning means. The fixing means can similarly fix the human or animal body comprising the tissue or organ of interest, the fixation of the latter leading de facto to the fixation of said target tissue or body structure.

6. Instrumented Analysis Chain

According to the present invention, there is provided but not shown in the drawing an instrumented analysis chain for determining the molecular composition of a determined location of a target tissue or another body structure of a human or animal body.

According to the present invention, the term "chain" relates to a series of instruments and/or apparatus connected causally and/or physically.

The chain comprises:
- a sampling instrument as above-described or a sampling apparatus as above-described for taking a sample in situ and in vivo or taking a sample ex vivo, and
- an analysis mean for determining the qualitative, possibly quantitative, molecular composition of said sample, said analysis mean having the sensitivity that corresponds with the quantity of the sample.

The analysis chain possibly comprises means for treating the sample captured and retained on said sampling instrument, said means for treating the sample excluding all disruption methods.

As already extensively explained and described above, different kinds of disruption methods exit. All these disruption methods are excluded from the method for determining the detailed composition of the target tissue or other body structure according to the present invention.

7. Kits

According to the present invention, there is provided a kit comprising the sampling instrument as above-described. The sampling instrument or means can be stored in the kit in sterilized condition.

8. Use of the Sampling Instrument

As shown by the following examples, the invention method according to the present invention has utility in various fields of biological analysis.

Preferably, the invention method finds numerous applications in the diagnosis or prognosis field.

According to the present invention, there is provided a method for revealing the presence of in situ molecular markers of a pathological state or a stage in the development of the disease of a patient, said pathological state or development stage being correlated to a tissue or other body structure, said method comprising the use of a sampling instrument or apparatus as mentioned in the present specification.

Examples of diseases which can be followed or monitored according to the present invention include, but are not limited to, patient cancers, tumors, neurodegenerative diseases, bacterial and viral infections. For instance, this method is used for revealing a molecular marker of the Parkinson's disease.

The relative amount of target molecules determined according to the present invention can be compared between groups of patients which are suffering from the same disease and patients which are not (controls), to determine possible biomarkers of the disease.

Knowledge of a biological system's response to a disease typically requires a comparison of many "normal" and "abnormal" samples. The sampling instrument of the present invention is thus useful to identify the potential molecular markers that distinguish normal from pathological state (for example malignant tissue) and to differentiate grades in the development of a disease.

EXAMPLES

The present invention is also described by means of particular examples. However, the use of such examples anywhere in the specification is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims.

In the following examples, the inventors have shown the technical feasibility of the method according to the present invention, within various target tissues or body structures of an animal or a human patient, and more particularly within the brain and liver of a rat, within the human brain (pathologic conditions of Parkinson's disease or dystonia), and in tumors affecting two different types of tissues (human lung and brain). These examples show the efficiency of the methods according to the present invention, as well as the scientific significance of such approaches, in particular in terms of diagnosis.

Figure 12:
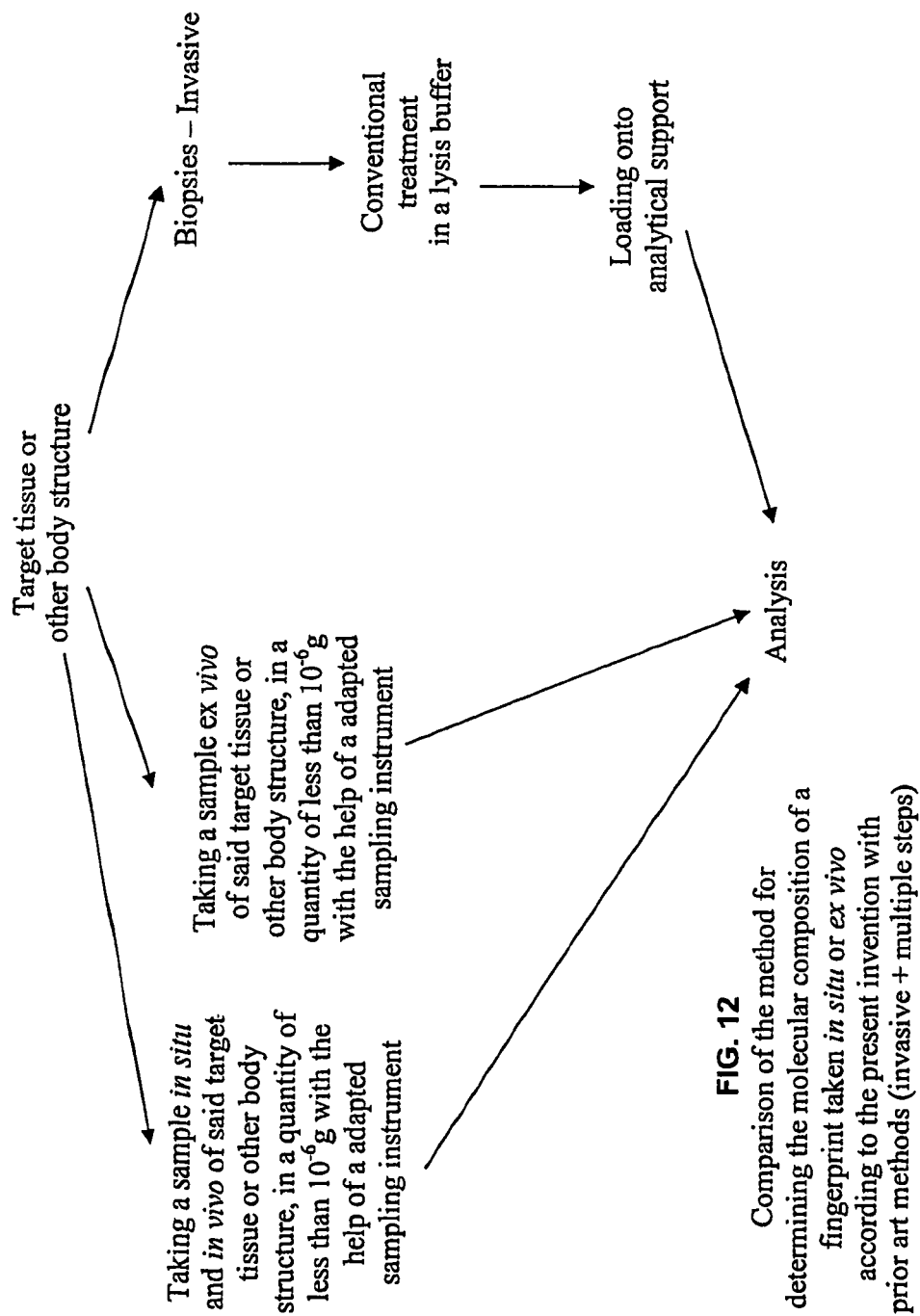

FIG. 12 shows, on the right hand side, the usual procedure using a biopsy.

The conventional protocol consists in solubilizing proteins by lysing cells and thus obtaining a lysate in an appropriate buffer. Next, after measuring out the proteins, the thus prepared sample is deposited on the analytical support (for example on Ciphergen ProteinChip arrays) and analyzed in an appropriate manner with the help of an analytical system (for example Ciphergen SELDI-TOF spectrometers).

As opposed to the conventional method, the hereinafter exemplified method according to the present invention consists in taking a sample in situ and in vivo, or ex vivo (as here above defined) by directly contacting the retaining surface of the active member of the sampling instrument with the target tissue or other body structure.

In this case, the biopsy or surgical sampling of a tissue fragment is not required. The biological compounds (in particular proteins, nucleic acids, metabolites, various organelles) which are within the analyzed organ are directly captured and fixed/retained by the retaining surface of the active member of the sampling instrument which will also be used as an analytical support by the appropriate analyzing device.

Example 1

Molecular Fingerprinting Using Sampling Instruments Inserted into Tissues (In Vivo Approach)

The tool used in the present example is hereafter described. It includes a guide for penetrating into the tissues and a sampling instrument. The distal operative end (ref 2 in FIG. 1) is a 200 mm-long hollow tube (or hollow tubular body), with a 2 mm-outside diameter (inside diameter 1.95 mm). It is used as a guide for inserting the sampling instrument into the tissue. This guide also includes a distal aperture (ref 31 in FIG. 1). When the sampling instrument is inserted into the hollow tubular body, the distal aperture enables the sampling instrument and the elementary retaining surfaces to contact the surrounding tissues. The sampling instrument is made of a stainless steel 250 mm-long metal rod, with a 1.9 mm diameter. It includes 5 elementary retaining surfaces (size of the elementary retaining surfaces: 1.9 mm and total length of retaining surface: 10 mm).

Use of the molecular fingerprinting instrument: The sampling instrument is introduced into the hollow tubular body until it stops. The instrument is oriented in the guide in such a way that the elementary retaining surfaces are oriented towards the inner side of the hollow tubular body (see FIG. 6). In the operating room, under appropriate surgery conditions, the created set or whole sampling instrument (hollow tubular body and sampling instrument as such, in the position as above defined) are inserted, through the skull of a patient, into the latter's brain. This is achieved by merely pushing the set along its main axis, into the organ. The penetration of the set is guided by very precise stereotactic marks, so that the distal aperture of the hollow tubular body is immobilized in the area of the ganglions of the base. The position of the set is mechanically blocked. The operator then rotates the sampling instrument within the hollow tubular body, while keeping the hollow tubular body perfectly still (see FIG. 5). The elongated active member is rotated by 180°. This action brings the sampling surfaces into contact with the neighbouring tissues. The sampling instrument is kept in that position for 30 seconds. During that period, the molecules (in particular the proteins) can adsorb onto the surface of each elementary retaining surface. Moreover, the existence of the various elementary retaining surfaces allows molecules to be collected at various depths of the penetrated tissue. At the end of the period when molecules are being adsorbed, the operator rotates the sampling instrument by 180°, in the opposite direction (which repositions the retaining surfaces within the guide, see FIG. 6). The sampling instrument is then withdrawn from the brain, in that position with regard to the hollow tubular body, and at the same time as the hollow tubular body. The sampling instrument which now has captured and retained the molecular fingerprints is then treated for analyzing the sampled molecules.

Treatment generally consists in immersing the retaining surfaces in a protein solubilization solution. The proteins which had been adsorbed on the surfaces are therefore freed from the retaining surface, due to this solution, and dissolved again in the latter.

Each surface is handled separately. The molecules sampled in areas of the brain which are different but close to one another are therefore collected independently. The stereotaxic sampling conditions allow for an extremely accurate prediction of the area of the brain in which each of the elementary retaining surfaces was when the molecular fingerprint was created.

For the molecules to be solubilized, the elementary retaining surfaces are mechanically separated (by breaking the sampling rod with cutting nippers). Each of the thus isolated, perfectly identified and marked elementary retaining surfaces is immersed into a solubilization solution; each elementary retaining surface is introduced into an Eppendorf tube containing 50 microliters of the solubilization solution which is composed of buffers, soft detergents and protease inhibitors—this solution is distributed by Promega (Reporter Lysis buffer into which protease inhibitors are extemporaneously added).

Alternatively, the individual solubilization of the molecules may be achieved by immersing the instrument into the solution according to the successive steps hereinafter described, instead of cutting the instrument. The retaining surface is immersed into a first tube containing 100 microliters of solution, so that only the elementary retaining surface which is at the furthest end of the elongated active member be immersed, for 10 min (this step allows for solubilization of only the proteins which are on the retaining surface at the end of the elongated active member). After this period of time, the elongated active member is immersed into a second tube containing 100 microliters of fresh solution, so that two elementary retaining surfaces be immersed, (the elementary retaining surface which is at the furthest end of the elongated active member, and its adjacent neighbour) for 10 min (this step allows for solubilization of the proteins which are on the retaining surface next to the one at the end of the rod). The elongated active member is then immersed into a third tube containing 100 microliters of solution, so that 3 elementary retaining surfaces be immersed, (the elementary retaining surface which is at the furthest end of the rod, and its two adjacent neighbours) for 10 min. This step is repeated as often as necessary, according to the number of elementary retaining surfaces.

The tubes used for solubilization are then centrifugated.
The continued protocol is as follows:
Centrifugation for 10 min at 4° C., then recovery of supernatant containing proteins in solution.

The presence of proteins in the buffer is then validated by analysis using the Ciphergen SELDI method (deposit of aliquot fractions on ProteinChips arrays and mass spectrometry analysis). 1 μL of this solution is deposited onto the SELDI arrays (reference of a type of array) and complemented up to 5 μL with binding buffer (the composition of the binding buffers used according to Ciphergen's recommendations).

Incubation for 15 min in a damp chamber at room temperature.

Removal of the buffer with a pipette and washes are carried out with the same buffer once or twice.

Short rinsing of the array in a 2 Mm HEPES buffer, then allowing it to dry for a few minutes.

2×0.8 μL of SPA matrix (sinapinnic acid matrix, 50% acetonitrile and 50% trifluoroacetic acid saturating solution) are deposited, allowing it to dry between the 2 deposits and this is allowed to dry thoroughly.

Reading the array on the spectrometer. Standard reading conditions as recommended by the manufacturer.

Mass spectra illustrate the result of multiple and simultaneous molecular detections reflecting the molecular complexity of the brain in various areas in the ganglions of the base. Sampling was carried out on 20 mm of tissue.

Example 2

Direct Use of the Instrument for Detecting Molecules, (No Desorption of the Molecules of the Fingerprinting Instrument)

In this example, the fingerprinting instrument or sampling instrument is composed of a thin silicon lamella whose surface is chemically modified. The surface can thus be modified for containing either carboxylic groups or amino groups which are covalently bonded to the silicon but remain available for chemical interactions with the environment. In the present example, the silicon rod is 0.8 mm wide, 0.3 mm thick and 2 cm long (distal operative end). The retaining surface is composed of carboxylic groups.

This silicon lamella was introduced into the brain of a rat.
Adhering this silicon lamella to the distal operative end gives a composite sampling instrument which may be used for molecular sampling in the brain of a patient according to the protocol mentioned in example here-above described.

After sampling, the silicon lamella is adhered to a metal array whose shape and dimensions are identical to those of Ciphergen's protein Biochips. This assembly is handled according to the protocol described hereinafter:

The silicium instrument is washed with binding buffer (the composition of the binding buffers used is according to Ciphergen's recommendations).

Incubation for 15 min in a damp chamber at room temperature.

Removal of the buffer with a pipette and washes are carried out with the same buffer once or twice.

Short rinsing of the array in a 2 Mm HEPES buffer, then allowing it to dry for a few minutes.

2×0.8 µL of SPA matrix (sinapinnic acid matrix, 50% acetonitrile and 0.5% trifluoroacetic acid saturating solution) are deposited, allowing it to dry between the 2 deposits and this is allowed to dry thoroughly.

Reading the array on the spectrometer. Standard reading conditions as recommended by the manufacturer Analysis is then carried out by inserting this array into the spectrometer. The silicon lamella is then irradiated by the laser beam of the spectrometer in spots of a very small size (diameter of the spot of the laser beam in the order of 100 microns). For each irradiated zone, a mass spectrum can thus be recorded and reflects the accurate composition of the molecular sample which has been adsorbed in a given area of the lamella. Since the position for irradiation can be chosen by the operator, a set of spectra (a minimum of 8 with a 4000 spectrometer) can thus be generated for each lamella. Knowledge of the illumination position by the laser beam enables a specific mass spectrum to be created for a given molecular sampling position in the tissue.

Examples 3 and 4 which follow show how obtaining molecular fingerprints by contacting an appropriate sampling instrument with an animal or human organ.

Examples 5 and 6 show the feasibility of the invention, on a tissue fragment taken on a patient, by direct molecular apposition of fresh tissue on the analytical support. The supports are finally analyzed with any ad hoc analyzing means. In these last examples, analyzing the lysates obtained after solubilization of the biological samples is carried out for reference purposes.

Example 3

Molecular Fingerprinting Using Sampling Instruments Inserted into Tissues (In Vivo Approach)

As shown in FIG. 13, three sampling instruments for electrically stimulating the specific anatomic regions of the brain of patients were implanted into the black substance (STN) of a patient's brain affected by Parkinson's disease (left on FIG. 13) or into the IGP (Internal Globus Pallidus) of a patient affected by dystonia (right on FIG. 13). The active members of said sampling instruments are inserted with the help of a hollow tubular member of said sampling instrument which prevents any contact between the active member of the sampling instrument and the brain tissues, before its implantation into the target determined location. After extraction of these active members of said sampling instruments by removal through the hollow tubular member of said sampling instrument, it has been shown that proteins were retained on the active distal part of the active member of the sampling instrument.

The protocol is as follows:

1. The retaining surface of the active members of said sampling instruments is dipped into a thin tube containing a non-ionic denaturant solution (buffer containing protease inhibitors, distributed by Promega, a company preparing kits for extracting and measuring out luciferase).

2. Incubation for 10 min at 4° C., then removal of these active members of said sampling instruments.

3. Centrifugation for 10 min at 4° C., then recovery of supernatant containing proteins in solution.

4. The presence of proteins in the buffer is then validated by analysis using the Ciphergen SELDI method (deposit of aliquot fractions on ProteinChips arrays and mass spectrometry analysis). 1 µL of this solution is deposited onto the SELDI arrays and complemented up to 5 µL with binding buffer (the composition of the binding buffers is adapted to the Protein-Chips used according to Ciphergen's recommendations).

5. Incubation for 15 min in a damp chamber at room temperature.

6. Removal of the buffer with a pipette and washes are carried out with the same buffer once or twice.

7. Short rinsing of the array in a 2 Mm HEPES buffer, then allowing it to dry for a few minutes.

8. 2×0.8 µL of SPA matrix (sinapinnic acid matrix) are deposited, allowing it to dry between the 2 deposits and this is allowed to dry thoroughly.

9. Reading the array on the spectrometer.

The various spectra shown in FIG. 13 correspond to the various lines obtained for the sampling instruments implanted into the STN or IGP regions. Analysis is carried out on ProteinChips with various chemical components distributed by Ciphergen (these arrays have active surfaces including polymer pellets with various chemical reactivity and capable of binding various biological compounds).

Spectra A were obtained using the SAX2 anionic array (ProteinChips, Ciphergen).

Spectra B were obtained using the NP20 hydrophile array (ProteinChips, Ciphergen).

Spectra C were obtained using the IMAC-Cu array (ProteinChips, Ciphergen).

Spectra D were obtained using the H50 hydrophobic array (ProteinChips, Ciphergen).

This result shows that proteins can be retained on sampling instruments which have been implanted onto determined locations of the brain. Analysis is sensitive, the lines obtained for various brain regions are specific for these regions.

Example 4

Molecular Fingerprinting by Direct Contact with a Rat Brain or a Rat Liver (Ex Vivo Approach)

In this example, a rat was killed, then the skull and abdomen were opened so as to widely expose the organs (brain and liver).

The modelling of the retaining surface of an active member of a sampling instrument according to the present invention was carried out by directly applying Ciphergen ProteinChips onto the organs. The direct contact between the array and the organ allows the typical biological compounds of the tissue to bind onto the arrays.

In this example, the arrays are of the anion-exchanger, SAX2 type, and the binding buffer contains TrisCl 100 mM pH 7.5.

Once they were removed from the organs, the arrays have undergone a conventional wash and impregnation procedure, so as to allow analysis of said arrays on the Ciphergen mass spectrometer, according to one of the two following protocols:

Preparation of Arrays in a Bioprocessor

1. The array is inserted into the bioprocessor.

2. 100 µL of binding buffer are deposited.

3. Incubation is carried out for 30 to 60 min at room temperature with agitation.

4. The buffer is removed and 2 washes are carried out with the same buffer.

5. The array is rinsed in 2 mM HEPES and allowed to dry for a few minutes.

6. 2×0.8 µL of SPA matrix (sinapinnic acid matrix) are deposited, allowing it to dry between the 2 deposits and this is allowed to dry thoroughly.

7. Reading the array on the spectrometer

Preparation of Arrays in Drops 1. 8 µL of binding buffer are deposited (according to the surface used).

2. Incubation is carried out for 15 min in a humid chamber at room temperature.

3. The buffer is removed with a pipette, and rinsing is carried out once or twice with the same buffer.

4. The array is rapidly rinsed in 2 mM HEPES buffer and allowed to dry for a few minutes.

5. 2×0.8 µL of SPA matrix are deposited, allowing it to dry between the 2 deposits and this allowed to dry thoroughly.

6. Reading the array on the spectrometer.

Figure 14:
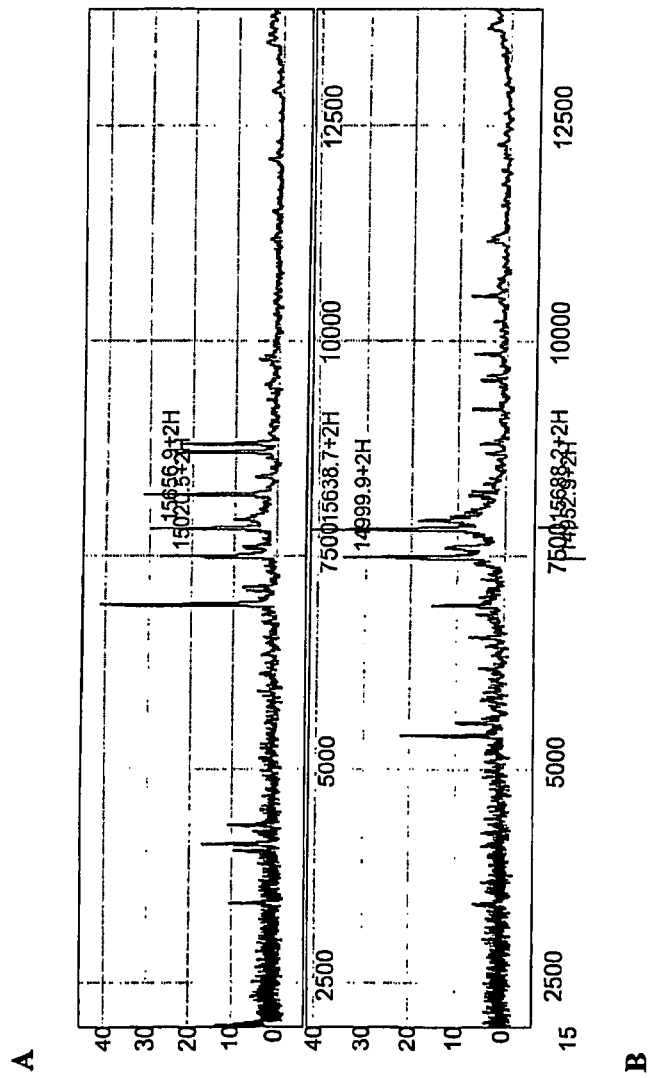
Figure 15:
Figure 16:
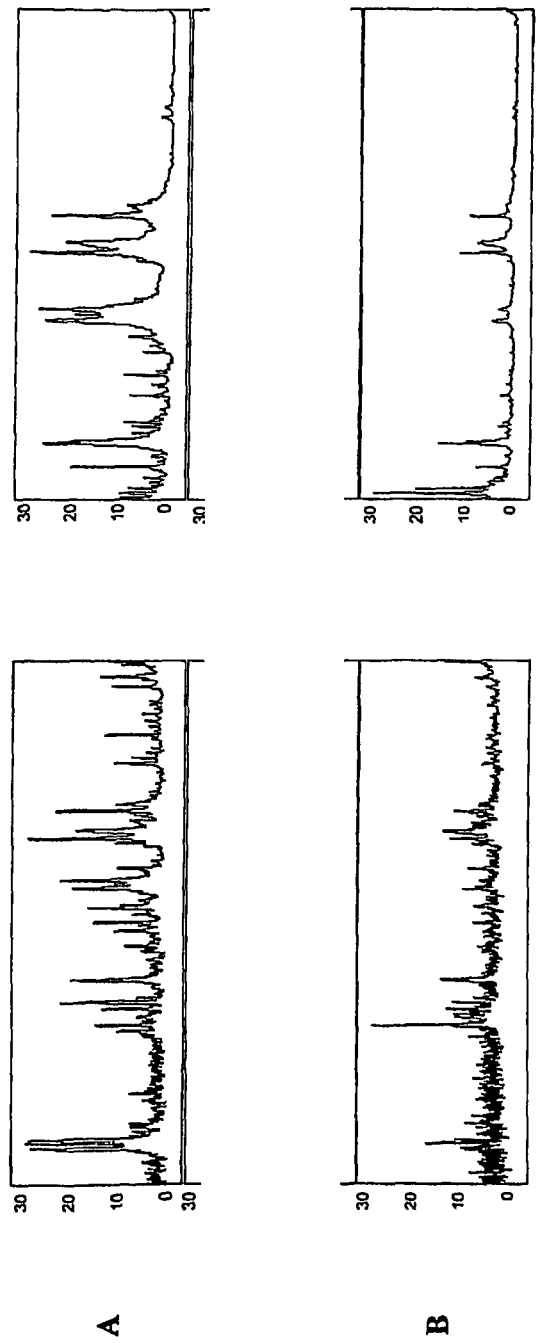

Results: see FIG. 14

(A) Rat Liver and (B) Rat Brain

In both cases, the obtained mass spectra show that proteins have been absorbed on the arrays upon direct contact between the arrays and the organ. Detection sensitivity is good, the patterns obtained for the liver differ from those of the brain. The created and analyzed fingerprint is specific for the tissue or organ on which the fingerprinting was performed. This test shows that it is possible to design retaining surface in the form of active member, the end surface of which can carry retaining surface protein chips of various chemical relativities, for repeated in vivo molecular fingerprinting with the help of a sampling instrument.

In the following examples, the tissue samples taken in the studied organs are used in three different manners:

(1) according to the conventional protocol, which consists in solubilizing proteins by creating a lysate which is used for detecting on ProteinChip arrays (Ciphergen);

(2) by ex vivo apposition of fresh tissue onto a ProteinChip array (Ciphergen); and Example 5

Molecular Fingerprinting on ProteinChip Arrays (Ciphergen) with Lysates, Appositions of Human Glioblastoma In this example, fingerprinting was carried out on a glioblastoma biopsy. The lysate, and apposition of fresh tissue are performed on the same type of ProteinChips.

A tumor biopsy is taken during a surgical operation of a brain tumor. The two protocols mentioned below are implemented. The molecular appositions are performed extemporaneously during the surgical operation.

Lysate Creation Protocol:

The biopsy samples are incubated in a lysis buffer.

They are then centrifuged at 10,000 g for 10 min at 4° C.

Next, aliquot fractions of lysis (supernatant of the previous step) are deposited onto the surface of the ProteinChips (Ciphergen) and are washed in drops or in a bioprocessor as mentioned above. The arrays are read in a Ciphergen SELDI-TOF spectrometer.

Apposition Protocol:

The fresh tissue is contacted for a few seconds with the ProteinChip array. Then the ProteinChip array is handled as mentioned above.

FIG. 15

Spectra A correspond to lysates.

Spectra B correspond to appositions.

As far as lysates are concerned, the number of visible peaks is more limited than for apposition. As a conclusion, the analysis of fresh tissue apposition appears to be a lot more sensitive than that of the lysate. Moreover, the fact that the patterns display many peaks, corresponding to small molecular weights (<10,000 Da), shows that the analysis of apposition allows for the detection of much more different peptides than the analysis of lysates. The inventors thereby prove the superiority of appositions and fingerprinting compared to the conventional lysate. Such results, represented by spectra, moreover show that target discovery research can be taken into consideration.

Example 6

Molecular fingerprinting on ProteinChip arrays (Ciphergen) with lysates, appositions of human bronchial adenocarcinoma The protocols of example 5 are repeated in a similar way for samples of bronchial adenocarcinoma.

FIG. 16

Spectra A correspond to appositions.

Spectra B correspond to lysates.

The conclusions are identical to those mentioned above. The analysis of appositions allows for a greater sensitivity and allows a greater quantity of small peptides to be spotted.

The invention claimed is:

1. A sampling instrument adapted for taking a sample in situ and in vivo or taking a sample ex vivo of a target tissue or body structure, in a maximum quantity of less than $10^{-6}$ g, said instrument comprising:

an elongated active member extending along an axis from a proximal end to a distal operative end, the active member presenting a back side extending along the axis, the distal operative end having at least one retaining surface angularly offset from the back side and arranged for contacting directly said target tissue or body structure, capturing and retaining molecules of said target tissue or body structure thereto, wherein the retaining surface comprises at least two elementary retaining surfaces separated by one of a rib and a collecting groove, the elementary retaining surfaces being arranged in sequence on the distal operative end along the axis of the active member, each elementary retaining surface being coated with a material adapted to bind molecules of the target tissue or body structure;

an elongated hollow component extending along an axis and in which the active member is movably mounted, the active member being movable in axial translation and in rotation about the axis of the active member inside the hollow component, the hollow component comprising a side wall extending along the axis of the hollow component, a proximal opening through which the active member is mounted in the hollow component, and a distal aperture opening into the side wall, the distal aperture being closed by the back side of the active member, when the active member engaged in the hollow component is in a first angular position relative to the hollow component, and being opened when the active member engaged in the hollow component is in a second angular position relative to the hollow component, the second angular position exhibiting the retaining surface of the active member through the distal aperture of the hollow component.

2. The sampling instrument of claim 1, wherein said retaining surface is arranged for contacting directly said target tissue or body structure, capturing and retaining proteins of said target tissue or body structure thereto.

3. The sampling instrument of claim 1, wherein the retaining surface comprises protein chips.

4. The sampling instrument of claim 1, further comprising: a proximal end; and a handle at the proximal end.

5. The sampling instrument of claim 1, wherein the distal operative end with the retaining surface is separable from the active member.

6. An apparatus comprising the sampling instrument of claim 1.

7. The apparatus of claim 6, further comprising: a source of liquid medium for separating and recovering the sample retained on said retaining surface.

8. The apparatus of claim 7, wherein the sampling instrument is adapted to contact said liquid medium with said sample, the active member of the sampling instrument having two positions relative to said elongated component, including:
  a first position in which said sample is captured and retained on said retaining surface, and
  a second position in which said retained sample is contacted with said liquid medium.

9. The apparatus of claim 7, further comprising a case distinct from and complementing the sampling instrument, the case being adapted to contact said liquid medium with said sample, the case comprising an aperture adapted to receive the distal operative end of the active member, at least one washing chamber which is closed when said retaining surface is positioned inside said chamber, and at least one aperture for introducing and removing said liquid medium in said washing chamber.

10. The apparatus of claim 6, further comprising: a location software and a mapping system for positioning the sampling instrument within said target tissue or body structure.

11. An instrumented analysis chain for determining the molecular composition of a determined location of a target tissue or body structure of a human or animal body, said chain comprising:
  a sampling instrument according to claim 1 for taking a sample in situ and in vivo or taking a sample ex vivo,
  an analytical device comprising one of a mass spectrometer, a fluorometer, an optical detector, mass fingerprinter, fluorescent or sensitive mass nano-detector, for determining the qualitative molecular composition of said sample, directly on it, said analytical device having a sensitivity consistent with the quantity of the sample.

12. The instrumented analysis chain of claim 11, wherein the analytical device is further adapted to determine the quantitative molecular composition of said sample, directly on it.

13. The sampling instrument according to claim 1, wherein an outer side of said retaining surface is adapted to contact said target tissue or said target body structure.

14. The sampling instrument according to claim 1, wherein said instrument is adapted for a penetration into said target tissue or body structure, and an inner side of said retaining surface is adapted to contact said target tissue or body structure.

15. The sampling instrument according to claim 1, wherein said instrument is disposable.

16. A method for determining a molecular composition of a target tissue or body structure comprising steps of providing a sampling instrument of claim 1 and of directly contacting said target tissue or body structure.

17. The sampling instrument of claim 1, wherein the instrument is adapted to take a sample in situ and in vivo or taking a sample ex vivo of a target tissue or body structure, in a quantity of less than $10^{-15}$ g.

18. A sampling instrument adapted for taking a sample in situ and in vivo or taking a sample ex vivo of a target tissue or body structure, said instrument comprising:
  an elongated active member extending along an axis from a proximal end to a distal operative end, the active member presenting a back side extending along the axis, the distal operative end having at least one retaining surface angularly offset from the back side and arranged for contacting directly said target tissue or body structure, capturing and retaining molecules of said target tissue or body structure, wherein the retaining surface is adapted to bind molecules of the target tissue or body structure; and
  an elongated hollow component extending along an axis and in which the active member is movably mounted, the active member being movable in axial translation and in rotation about the axis of said active member inside the hollow component, the hollow component comprising a side wall extending along the axis of said hollow component, a proximal opening through which the active member is mounted in the hollow component, and a distal aperture opening into the side wall, wherein the distal aperture is delimited by two longitudinal edges of the side wall extending along the axis of the hollow component in a plane, wherein the distal aperture is closed by the back side of the active member, when the active member engaged in the hollow component is in a first angular position relative to the hollow component, and being opened when the active member engaged in the hollow component is in a second angular position relative to the hollow component, the second angular position exhibiting the retaining surface of the active member through the distal aperture of the hollow component,
  wherein in the second angular position, the retaining surface of the active member lies substantially within the plane of the longitudinal edges of the side wall of the hollow component.

19. A sampling instrument adapted for taking a sample in situ and in vivo or taking a sample ex vivo of a target tissue or body structure, said instrument comprising:
  an elongated active member extending along an axis from a proximal end to a distal operative end, the active member presenting a back side extending along the axis, the distal operative end having at least one retaining surface angularly offset from the back side and arranged for contacting directly said target tissue or body structure, capturing and retaining molecules of said target tissue or body structure, wherein the retaining surface is adapted to bind molecules of the target tissue or body structure; and
  an elongated hollow component extending along an axis and in which the active member is movably mounted, the active member being movable in axial translation and in rotation about the axis of said active member inside the hollow component, the hollow component comprising a side wall extending along the axis of said hollow component, a proximal opening through which the active member is mounted in the hollow component, and a distal aperture opening into the side wall, the distal aperture being closed by the back side of the active member, when the active member engaged in the hollow component is in a first angular position relative to the hollow component, and being opened when the active member engaged in the hollow component is in a second angular position relative to the hollow component, the second angular position exhibiting the retaining surface of the active member through the distal aperture of the hollow component, wherein the sampling instrument has a diameter lower than 3 mm.

20. A sampling instrument adapted for taking a sample in situ and in vivo or taking a sample ex vivo of a target tissue or body structure, said instrument comprising:

an elongated active member comprising a sampling rod extending along an axis from a proximal end to a distal operative end, the active member presenting a back side extending along the axis, the distal operative end having at least one retaining surface angularly offset from the back side and arranged for contacting directly said target tissue or body structure, capturing and retaining molecules of said target tissue or body structure, wherein the retaining surface comprises at least one elementary retaining surface adapted to bind molecules of the target tissue or body structure, the elementary retaining surface being separable from the sampling rod; and an elongated hollow component extending along an axis and in which the active member is movably mounted, the active member being movable in axial translation and in rotation about the axis of said active member inside the hollow component, the hollow component comprising a side wall extending along the axis of said hollow component, a proximal opening through which the active member is mounted in the hollow component, and a distal aperture opening into the side wall, the distal aperture being closed by the back side of the active member, when the active member engaged in the hollow component is in a first angular position relative to the hollow component, and being opened when the active member engaged in the hollow component is in a second angular position relative to the hollow component, the second angular position exhibiting the retaining surface of the active member through the distal aperture of the hollow component.

21. A sampling instrument adapted for taking a sample in situ and in vivo or taking a sample ex vivo of a target tissue or body structure, said instrument comprising:

an elongated active member extending along an axis from a proximal end to a distal operative end, the active member presenting a back side extending along the axis, the distal operative end having at least one retaining surface angularly offset from the back side and arranged for contacting directly said target tissue or body structure, capturing and retaining molecules of said target tissue or body structure, wherein the retaining surface is adapted to bind molecules of the target tissue or body structure; and an elongated hollow component extending along an axis and in which the active member is movably mounted, the active member being movable in axial translation and in rotation about the axis of said active member inside the hollow component, the hollow component comprising a side wall extending along the axis of said hollow component, a proximal opening through which the active member is mounted in the hollow component, and a distal aperture opening into the side wall, wherein the distal aperture is delimited by two longitudinal edges of the side wall extending along the axis of the hollow component in a plane, wherein the distal aperture is closed by the back side of the active member, when the active member engaged in the hollow component is in a first angular position relative to the hollow component, and being opened when the active member engaged in the hollow component is in a second angular position relative to the hollow component, the second angular position exhibiting the retaining surface of the active member through the distal aperture of the hollow component, wherein in the second angular position, the retaining surface of the active member lies substantially within the plane of the longitudinal edges of the side wall of the hollow component, and wherein the sampling instrument has a diameter lower than 3 mm.

* * * * *